United States Patent [19]

Hefner, Jr. et al.

[11] Patent Number: 5,428,125
[45] Date of Patent: Jun. 27, 1995

[54] MESOGENIC POLYCYANATES AND THERMOSETS THEREOF

[75] Inventors: Robert E. Hefner, Jr.; Jimmy D. Earls; Paul M. Puckett, all of Lake Jackson, Tex.

[73] Assignee: The Dow Chemical Company, Midland, Mich.

[21] Appl. No.: 261,649

[22] Filed: Jun. 17, 1994

Related U.S. Application Data

[63] Continuation of Ser. No. 91,460, Jul. 13, 1993, abandoned, which is a continuation of Ser. No. 907,993, Jul. 2, 1992, abandoned, which is a continuation-in-part of Ser. No. 746,527, Aug. 16, 1991, abandoned, which is a continuation-in-part of Ser. No. 380,938, Jul. 17, 1989, abandoned.

[51] Int. Cl.⁶ .................................................. C08G 73/10
[52] U.S. Cl. ................... 528/422; 525/540; 526/262; 526/285; 526/286; 526/312; 528/116; 528/117; 528/118; 528/119; 528/121; 528/172; 528/190; 528/192; 528/205; 528/211; 528/271; 528/322; 528/391; 528/392
[58] Field of Search ............... 528/422, 116, 117, 118, 528/119, 121, 172, 190, 192, 205, 211, 271, 322, 391, 392; 525/540; 526/262, 285, 286, 312

[56] References Cited

U.S. PATENT DOCUMENTS

| | | |
|---|---|---|
| 3,448,079 | 6/1969 | Grig et al. . |
| 3,491,060 | 1/1970 | Schminke et al. . |
| 3,498,981 | 3/1970 | Culbertson . |
| 3,502,617 | 3/1970 | Schminke et al. . |
| 3,553,244 | 1/1971 | Grig et al. . |
| 3,574,737 | 4/1971 | Grig et al. . |
| 3,642,725 | 2/1972 | Schminke et al. . |
| 3,694,410 | 9/1972 | Ochmke . |
| 3,740,348 | 6/1973 | Grigat et al. . |
| 3,755,402 | 8/1973 | Grigat et al. . |
| 3,876,607 | 4/1975 | Snell et al. . |
| 3,978,028 | 8/1976 | Sundermann et al. . |
| 3,994,949 | 11/1976 | Meyer et al. . |
| 4,042,567 | 8/1977 | Sundermann . |
| 4,046,796 | 9/1977 | Rottoloff et al. . |
| 4,059,567 | 11/1977 | Sundermann et al. . |
| 4,066,577 | 1/1978 | Sundermann et al. . |
| 4,094,852 | 6/1978 | Sundermann et al. . |
| 4,094,861 | 6/1978 | Sundermann et al. . |
| 4,097,455 | 6/1978 | Burkhardt et al. . |
| 4,110,364 | 8/1978 | Gaku et al. . |
| 4,157,360 | 7/1979 | Prevorsek et al. . |
| 4,195,132 | 3/1980 | Sundermann et al. . |
| 4,287,014 | 9/1981 | Gaku et al. . |
| 4,330,669 | 5/1982 | Ikeguchi et al. . |
| 4,369,304 | 1/1983 | Gaku et al. . |
| 4,370,467 | 1/1983 | Gaku et al. . |
| 4,371,689 | 2/1983 | Gaku et al. . |
| 4,373,086 | 2/1983 | Ikeguchi . |
| 4,383,903 | 5/1983 | Ayano et al. . |
| 4,389,516 | 6/1983 | Sugio et al. . |
| 4,393,195 | 7/1983 | Gaku et al. . |
| 4,396,745 | 8/1983 | Ikeguchi . |
| 4,404,330 | 9/1983 | Ikeguchi . |

(List continued on next page.)

FOREIGN PATENT DOCUMENTS 0295381  12/1988  European Pat. Off. .
60-94422   5/1985  Japan .

OTHER PUBLICATIONS

Chemical Abstract 91:123577e Biphenyl esters (Jpn. Kokai Tokkyo Koho 79 41,852) Mar. 1979.
Chemical Abstract 93:228647x Liquid crystal display devices (Jpn. Kokai Tokkyo Koho 8065,927) Jul. 1978.
Chemical Abstract 105:98544q Aromatic biscyanates (Jpn. Kokai Tokkyo Koho JP 61 76,450) Apr. 1986.
Chemical Abstract 111:7873f Polymeric and monomeric aryloxy-s-triazines.
'Advanced Materials and Processes' p. 12, Jul. 1991.

Primary Examiner—Joseph L. Schofer
Assistant Examiner—John M. Cooney, Jr.

[57] ABSTRACT

Novel polycyanate and polycyanamide compositions containing one or more rodlike mesogenic moieties, when cured, result in products having improved properties.

2 Claims, No Drawings

U.S. PATENT DOCUMENTS

| | | |
|---|---|---|
| 4,414,366 | 11/1983 | Wu et al. |
| 4,469,859 | 9/1984 | Gaku et al. |
| 4,477,629 | 10/1984 | Hefner, Jr. |
| 4,486,583 | 12/1984 | Takahashi et al. |
| 4,528,366 | 7/1985 | Woo et al. |
| 4,544,704 | 10/1985 | Hefner, Jr. |
| 4,554,346 | 11/1985 | Gali et al. |
| 4,555,563 | 11/1985 | Hefner, Jr. et al. |
| 4,558,115 | 12/1985 | Hefner, Jr. |
| 4,559,399 | 12/1985 | Hefner, Jr. |
| 4,578,439 | 3/1986 | Hefner, Jr. |
| 4,581,425 | 4/1986 | Hefner, Jr. |
| 4,585,855 | 4/1986 | Gaku et al. |
| 4,600,760 | 7/1986 | Hefner, Jr. |
| 4,604,452 | 8/1986 | Shimp |
| 4,607,094 | 8/1986 | Sugawara et al. |
| 4,608,434 | 8/1986 | Shimp |
| 4,631,319 | 12/1986 | Blahak et al. |
| 4,665,154 | 5/1987 | Varnell et al. |
| 4,680,378 | 7/1987 | Hefner, Jr. |
| 4,683,276 | 7/1987 | Hefner, Jr. |
| 4,709,008 | 11/1987 | Shimp |
| 4,713,442 | 12/1987 | Woo et al. |
| 4,731,426 | 3/1988 | Hefner, Jr. |
| 4,738,900 | 4/1988 | Ono et al. |
| 4,740,584 | 4/1988 | Shimp |
| 4,745,215 | 5/1988 | Cox et al. |
| 4,746,727 | 5/1988 | Bogan et al. |
| 4,749,760 | 6/1988 | Wang |
| 4,751,323 | 6/1988 | Woo et al. ............ 528/271 |
| 4,754,001 | 6/1988 | Blahak et al. |
| 4,769,440 | 9/1988 | Hefner |
| 4,774,282 | 9/1988 | Zureshi |
| 4,774,316 | 9/1988 | Godschalx et al. |
| 4,777,226 | 10/1988 | Holte |
| 4,782,116 | 11/1988 | Holte |
| 4,785,075 | 11/1988 | Shimp |
| 4,806,625 | 2/1989 | Bogan et al. |
| 4,839,460 | 6/1989 | Molzahn |
| 4,851,279 | 7/1989 | Das et al. |
| 4,861,823 | 8/1989 | Qureshi |
| 4,946,928 | 8/1990 | Jackson et al. |
| 4,962,163 | 10/1990 | Herner, Jr. et al. ............ 526/286 |
| 4,978,727 | 12/1990 | Das et al. |
| 4,983,709 | 1/1991 | Jackson |
| 4,988,780 | 1/1991 | Das et al. |
| 5,024,785 | 6/1991 | Hefner, Jr. et al. ............ 525/502 |
| 5,077,300 | 12/1991 | Hefner, Jr. et al. |
| 5,077,380 | 12/1991 | Hefner, Jr. ............ 528/117 |
| 5,136,011 | 8/1992 | Barclay et al. |
| 5,154,030 | 10/1992 | Hefnar, Jr. et al. ............ 526/285 |

MESOGENIC POLYCYANATES AND THERMOSETS THEREOF

CROSS-REFERENCE TO RELATED APPLICATION

This is a continuation of application Ser. No. 08/091,460 filed Jul. 13, 1993, now abandoned, which is a continuation of application Ser. No 907,993, filed Jul. 2, 1992, now abandoned, which is a continuation-in-part of application Ser. No. 07/746,527 filed Aug. 16, 1991, now abandoned which is a continuation-in-part of now abandoned, application Ser. No. 07/380,938 filed Jul. 17, 1989, all of which are incorporated herein by reference in their entirety.

FIELD OF THE INVENTION

The present invention concerns polycyanates (polycyanamides) containing one or more rodlike mesogenic moieties.

BACKGROUND OF THE INVENTION

Aromatic polycyanates which are thermosettable to polytriazines are known, for example, from U.S. Pat. Nos. 3,448,079; 3,553,244; 3,694,410; 3,740,348; 3,755,402; 4,094,852 and 4,097,455. Said polytriazines possess excellent heat resistance, however, an improvement in their mechanical properties, especially tensile and flexural strength, tensile and flexural modulus and tensile elongation while maintaining or even increasing glass transition temperature, would be desirable. The present invention provides a method for improving one or more of the aforementioned properties by incorporation into the polymer chains of the polytriazines one or more rodlike mesogenic structure(s). Incorporation of said rodlike mesogenic structures can lead to a molecular level ordering of the polytriazine thermoset thereof. The present invention also provides polymerizable mixtures containing one or more of the polycyanates (polycyanamides) containing rodlike mesogenic structure(s) with, for example, one or more polycyanates (polycyanamides) which do not contain rodlike mesogenic moieties, epoxy resins, polymaleimides, polyamines, polyphenols, polymerizable ethylenically unsaturated compounds, compounds which simultaneously contain both a cyanate or cyanamide group and a polymerizable ethylenically unsaturated group, compounds which simultaneously contain both a 1,2-epoxide group and a polymerizable ethylenically unsaturated group, compounds which simultaneously contain both a maleimide group and a cyanate or cyanamide group and materials which contain one or more rodlike mesogenic structure(s) and an average of one cyanate or cyanamide group per molecule. The thermoset compositions prepared from the aforementioned polymerizable mixtures typically possess improvements in physical and mechanical properties relative to those thermoset compositions prepared using polycyanates (polycyanamides) which do not contain rodlike mesogenic structure(s).

Certain of the polycyanates containing rodlike mesogenic structure(s) exhibit novel thermally induced self-curing behavior at onset temperatures much lower than those encountered with the polycyanates which do not contain rodlike mesogenic structure(s). Two distinct variations of this modified curing behavior are provided: As a specific example, when the azomethine group (—CH=N—) is present as a rodlike mesogenic structure, it can lower the onset temperature to curing without participating in the formation of the curing structure of the thermoset product. As a second example, when the secondary amide group (—NH—CO—) is present, it too can lower the onset temperature to curing, but appears to participate in the formation of the curing structure of the thermoset product via reaction of the amide proton. When used as a component in the polymerizable mixtures of the present invention, these same polycyanates can often be used to reduce the onset temperature required to cure (thermoset) said mixture.

SUMMARY OF THE INVENTION

The present invention pertains to polycyanate or polycyanamide compositions containing one or more rodlike mesogenic moieties, particularly those represented by the following Formulas I, II, III or IV

Formula I

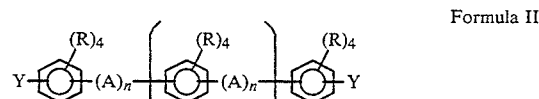

Formula II

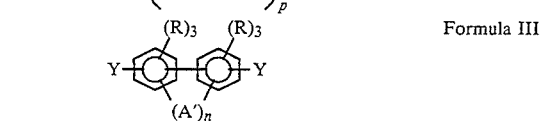

Formula III

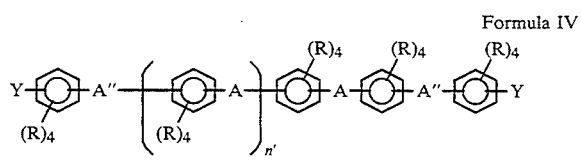

Formula IV wherein at least about 80 percent of the —A— linkages, the direct bond in Formula III and the Y groups are in the para position with respect to each other; each Y is independently a —O—C≡N or a —NR$^1$—C≡N group; each A is independently —CR$^1$=CR$^1$—, —C≡C—, —N=N—, —CR$^1$=N—, —O—CO—, —NR$^1$—CO—, —CR$^1$=N—N=CR$^1$—, —CR$^1$=CR$^1$—O—, —CO—O—, —CO—NR$^1$—, —CO—CR$^1$=CR$^1$—, —CR$^1$=CR$^1$—O—CO—(CH$_2$)$_{n'}$—, —N=CR$^1$—, —(CH$_2$)$_{n'}$—CO—O—CR$^1$=CR$^1$—, —CR$^1$=CR$^1$—O—CO—, —CO—O—CR$^1$=CR$^1$—, —CO—O—N=CR$^1$—, —CR$^1$=N—O—CO—, —CR$^1$=CR$^1$—CO—O—, —CO—S—, —O—CO—CR$^1$=CR$^1$—, —CR$^1$=CR$^1$—CO—O—(CH$_2$)$_{n'}$—, —S—CO—, —(CH$_2$)$_{n'}$—O—CO—CR$^1$=CR$^1$—, —CHR$^1$—CHR$^1$—CO—O—, —O—CO—CHR$^1$—CHR$^1$—, —C≡C—C≡—C—, —CR$^1$=CR$^1$—CR$^1$=CR$^1$—, —CO—NR$^1$—NR$^1$—CO—,

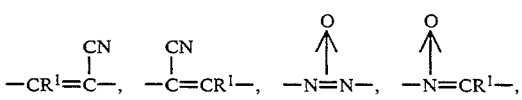

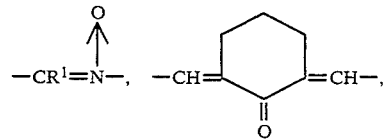

A' is a divalent hydrocarbyl group having from 1 to about 10, preferably from 1 to about 4, carbon atoms; each A" is independently an alkylene group having from 1 to about 10 carbon atoms, preferably from 1 to about 4 carbon atoms, a direct bond, —O—, —CO—, —S—, —S—S—, —SO—, —SO₂— or —O—CO—O—; each A¹ is independently a —CO—, —O—CO—, —CO—O—, —CO—NR¹—, or —NR¹—CO— group; each R is independently hydrogen or a hydrocarbyl or hydrocarbyloxy group having from 1 to about 10, preferably from 1 to about 4, carbon atoms, a halogen atom, preferably chlorine or bromine, a nitro group, a nitrile group, a phenyl group or a —CO—R¹ group; each R¹ is independently hydrogen or a hydrocarbyl group having 1 to about 3 carbon atoms; v has a value of one or two; n has a value of zero or one; n' has a value from 1 to about 6, preferably 1 to about 3; p has a value from 1 to about 30, preferably from 1 to about 3; and not including 4,4'-dicyanatostilbene, 4,4'-dicyanamidoazobenzene, 4,4'-dicyanamidobenzanilide, 4,4'-dicyanamidophenyl benzoate, dicyanates of the diphenol esters of terephthalyl chloride and bisphenol A, 4,4'-dihydroxydiphenyl, and dicyanates represented by the following formulas

wherein Ar is an aromatic radical selected from the group consisting of 1,4-benzene, 1,4-naphthalene, 1,5-naththalene, 2,6-naphthalene, 2,7-naphthalene, 4,4'-biphenyl, 4,4'-diphenylalkylene radicals and can possess any nonactive hydrogen-containing substituent(s) which do not remove mesogenicity. The aromatic rings can also contain one or more heteroatoms such as N, O or S and the like.

The term mesogen is defined by R. A. Weiss (ed.) and C. R. Ober (ed.) in *Liquid-Crystalline Polymers*, ACS Symposium Series 435 (1989) on page 2: "The rigid unit responsible for the liquid crystalline behavior is referred to as the mesogen." and "Liquid crystalline order is a consequence solely of molecular shape anisotropy, such as found in rigid rod-shaped molecules . . . ". Further definition of the term mesogen may be found in *Polymeric Liquid Crystals*, Alexandre Blumstein (ed.) (1983) on pages 2–3 and in *Polymeric Liquid crystals*, A. Ciferri, W. R. Krigbaum and Robert B. Meyer (eds.) (1982) on pages 5–9, both of which are incorporated herein by reference.

Thus, while the dicyanate, 1,4-bis(p-cyanatophenyl)-cyclohexane is mesogenic and thus a composition of the present invention, 1,1-bis(p-cyanatophenyl)cyclohexane is not mesogenic and is thus not a composition of the present invention, due to the 1,1-disubstitution of the cyclohexane ring which leads to a highly bent structure. The dicyanates of 1,4-bis(4'-hydroxyphenyl)propyl)-benzene, 2,2-bis(3',5'-dimethyl-4'-hydroxyphenyl)propane, 2,2-bis(4'-hydroxyphenyl-1,1,1,3,3,3-hexafluoro-propane) and 9,9-(bis(4-hydroxyphenyl)fluorene are likewise not compositions of the present invention because they do not possess the proper molecular shape anisotropy required for mesogenicity to exist.

Woo and Murray in U.S. Pat. No. 4,751,323, which is incorporated herein by reference in its entirety, disclose polyaromatic cyanates of the general formula

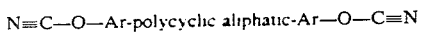

where Ar refers to any radical containing an aromatic group and may possess any nonactive hydrogen-containing substituent(s). The polycyclic aliphatic radicals include

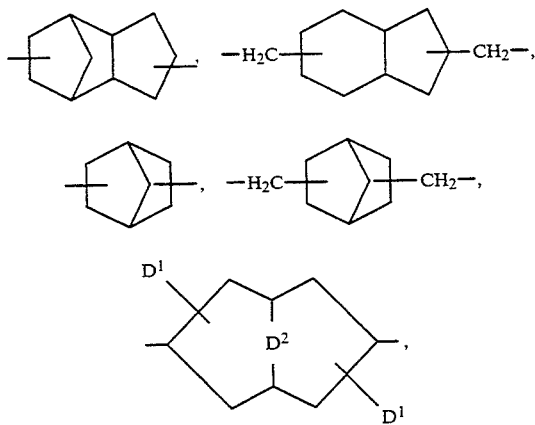

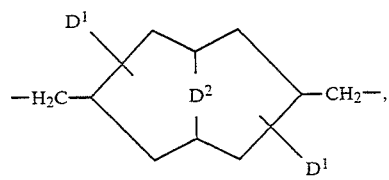

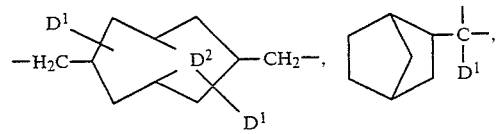

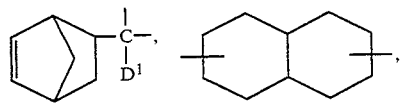

wherein $D^1$ is a $C_{1-5}$ alkyl group and $D^2$ is —$CH_2$—, —S—, —SO—, or —$SO_2$—. These compounds do not possess the proper molecular shape anisotropy for mesogenicity to exist and are thus not compositions of the present invention. As a specific example, 1,4-bis(p-cyanatophenyl) substituted

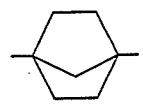

possesses the proper molecular shape anisotropy to be mesogenic and is thus a composition of the present invention, while 1,4-bis(p-cyanatophenyl) substituted

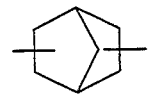

does not, and is thus not a composition of the present invention.

The term hydrocarbyl as employed herein means any aliphatic, cycloaliphatic, aromatic, aryl substituted aliphatic or cycloaliphatic, or aliphatic or cycloaliphatic substituted aromatic groups. The aliphatic or cycloaliphatic groups can be saturated or unsaturated. When applied to the A' group of Formula III, the hydrocarbyl group can also contain one or more heteroatoms selected from N, O, S and the like. Likewise, the term hydrocarbyloxy means a hydrocarbyl group having an oxygen linkage between it and the carbon atom to which it is attached.

Another aspect of the present invention pertains to compositions resulting from curing (thermosetting) one or more of the polycyanates or polycyanamides containing one or more rodlike mesogenic moieties, optionally in the presence of one or more curing agents or curing catalysts.

Another aspect of the present invention is directed to polymerizable compositions comprising a mixture containing (A) at least one thermosettable polycyanate or polycyanamide containing one or more rodlike mesogenic moieties; and
(B) at least one of
  (1) at least one polycyanate or polycyanamide which does not contain rodlike mesogenic structures;
  (2) at least one epoxy resin;
  (3) at least one polymaleimide;
  (4) at least one polyamine;
  (5) at least one polyphenol;
  (6) at least one compound containing one or more polymerizable ethylenically unsaturated group(s);
  (7) at least one compound which contains in the same molecule both a cyanate or cyanamide group and a polymerizable ethylenically unsaturated group;
  (8) at least one compound which contains in the same molecule both a 1,2-epoxide group and a polymerizable ethylenically unsaturated group;
  (9) at least one compound which contains in the same molecule both a maleimide group and a cyanate group;
  (10) at least one compound which contains one or more rodlike mesogenic moieties and only one cyanate or cyanamide group per molecule;
  (11) at least one prepolymer of any of the aforesaid components (1) through (10) or any combination of any two or more of said components; or
  (12) a mixture of any two or more of components (1) through (11) in any proportion and any combinations, with the proviso that component (A) may include 4,4'-dicyanatostilbene (Formula I, R=—H, Y=—O—C≡N, A=—CH=CH—) if components (B-4) or (B-5) are not used and with the proviso that component (A) may include 4,4'-dicyanamidoazobenzene (Formula I, R=—H, Y=—NH—C≡N, A=—N=N—), 4,4'-dicyanamidobenzanilide (Formula I, R=—H, Y=—NH—C≡N, A=—NH—CO—) or 4,4'-dicyanamidophenylbenzoate (Formula I, R=—H, Y=—NH—C≡N, A=—CO—O—) if components (B-3) or (B-4) are not used and with the proviso that component (A) may include the compositions of Formula IV where R is —H or —CH$_{13}$, $n=1$, Y=—O—C≡N, A" is as hereinbefore defined, where both A groups may simultaneously be —O—CO— and with the proviso that component (A) can include the 1,4-bis(p-cyanotophenyl)bicyclo[2.2.2]-octanes (Formula I, R=—H, a hydrocarbyl or hydrocarbyloxy group having from 1 to about 10 carbon atoms, or halogen atoms a nitro groups a nitrile group, a phenyl group or a —CO—R$^1$ group where R$^1$ is hydrogen or a hydrocarbyl group having 1 to about 3 carbon atoms; Y=—O—C≡N;

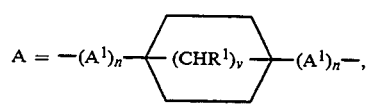

where $n=0$, $v=2$ and R$^1$=—H if component (B-1) is not used and with the proviso that component (A) can include the 1,4-bis(p-cyanatophenyl)bicyclo[2.2.2]oct-2-enes (Formula I, R=—H, a hydrocarbyl or hydrocarbyloxy group having from 1 to about 10 carbon atoms, a halogen atom, a nitro group, a nitrile group, a phenyl group or a —CO—R$^1$ group where R$^1$ is hydrogen or a hydrocarbyl group having from 1 to about 3 carbon atoms; Y=—O—C≡N; A=

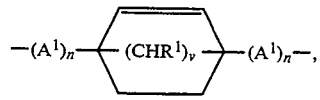

where $n=0$, $v=2$ and R$^1$=—H if component (B-1) is not used.

Another aspect of the present invention pertains to compositions resulting from polymerizing the aforementioned polymerizable compositions.

A further aspect of the present invention pertains to products resulting from orienting any of the aforementioned polymerizable compositions.

The term prepolymers as employed herein means that the compound has been homopolymerized or cooligomerized or interoligomerized or homopolymerized or copolymerized or interpolymerized so as to cause an increase in molecular weight, but not to such an extent that the product has become cured, i.e. insoluble and infusible, but rather, the product is capable of being subsequently cured to an insoluble, infusible state.

These compounds can also contain substituent groups such as saturated aliphatic hydrocarbon, unsaturated aliphatic hydrocarbon, halogens including chlorine bromine, fluorine, iodine, nitro, nitrile, and the like. Likewise, the hydrocarbon substituent groups can also be substituted with such halogens including chlorine bromine, fluorine, iodine, nitro, nitrile, and the like. Also, these compounds can be specifically free of any one or more of such substituent groups and likewise the substituted hydrocarbons can be specifically free of any one or more of such substituent groups. Further, such compounds and substituted hydrocarbons can contain any substituent group not specifically enumerated herein. Likewise, the compounds and substituted hydrocarbons can be free of any substituent group not specifically enumerated herein.

The present invention may suitably comprise, consist of, or consist essentially of, the aforementioned components.

The invention illustratively disclosed herein suitably may be practiced in the absence of any component which is not specifically disclosed or enumerated herein and any of the compounds may contain or be free of any substitutent not specifically named herein.

DETAILED DESCRIPTION OF THE INVENTION

PREPARATION OF THE POLYCYANATES OR POLYCYANAMIDES CONTAINING ONE OR MORE RODLIKE MESOGENIC MOIETIES

The polycyanates or polycyanamides of the present invention are prepared by reacting one or more of the polyphenols, polyamines or aminophenols containing one or more rodlike mesogenic moieties with a stoichiometric quantity or a slight stoichiometric excess (up to about 20 percent excess) of a cyanogen halide per —OH or —NHR$^1$ group in the presence of a stoichiometric quantity or a slight stoichiometric excess (up to about 20 percent excess) of a base compound per —OH or —NHR$^1$ group and in the presence of a suitable solvent.

Reaction temperatures of from about −40° C. to about 60° C. are operable, with reaction temperatures of −15° C. to 10° C. being preferred. Reaction times can vary substantially, for example, as a function of the reactants being employed, the reaction temperature, solvent(s) used, the scale of the reaction, and the like, but are generally between 15 minutes and 4 hours, with reaction times of 30 minutes to 90 minutes being preferred.

Suitable polyphenols, polyamines or aminophenols which can be employed herein to prepare the polycyanates or polycyanamides containing one or more rod-like mesogenic moieties include, for example, any compound which has an average of more than one aromatic hydroxyl group, aromatic primary or secondary amino group or a combination of said hydroxyl and amino groups per molecule and include, for example, those represented by the Formulas V, VI, VII or VIII wherein at least about 80 percent of the —A— linkages in Formulas V, VI and VIII and the direct bond between the two aromatic rings in Formula VII and the $Y^1$ groups are in the para position with respect to each other; each $Y^1$ is independently a —OH or —$NHR^1$ group; each A, A′, A″, $A^1$, R, $R^1$, v, n, n′ and p are as hereinbefore defined. The aromatic rings can also contain one or more heteroatoms selected from N, O, S and the like.

Particularly suitable polyphenols are 4,4′-dihydroxy-alpha-methylstilbene, 4,4′-dihydroxychalcone, 4,4′-dihydroxydiphenylacetylene, 4,4′-dihydroxydiphenylazomethine, 4,4′-dihydroxyazobenzene, 4,4′-dihydroxyazoxybenzene, 4,4′-bis(4-hydroxyphenoxy)-diphenyl, 4,4′-dihydroxy-alpha-cyanostilbene, 4,4′-dihydroxybenzanilide, 4-hydroxyphenyl-4-hydroxybenzoate,

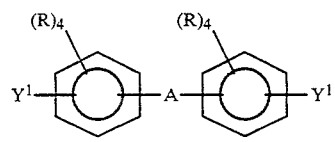

Formula V

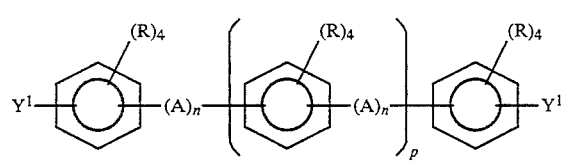

Formula VI

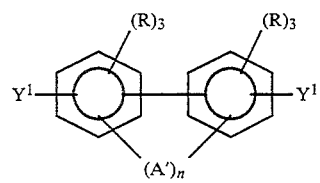

Formula VII

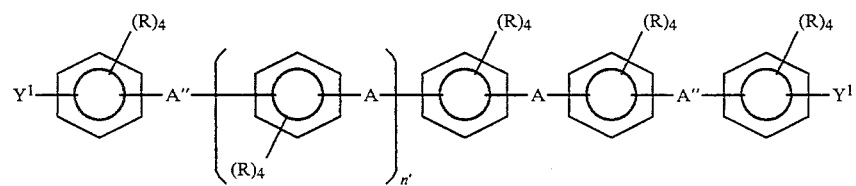

Formula VIII

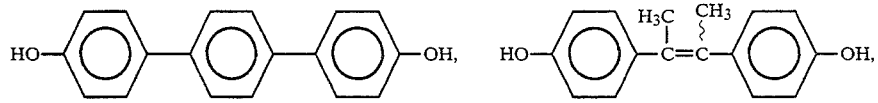
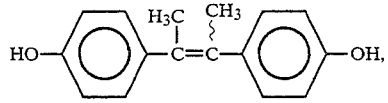

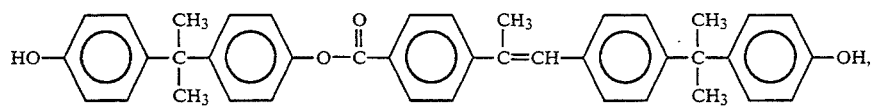

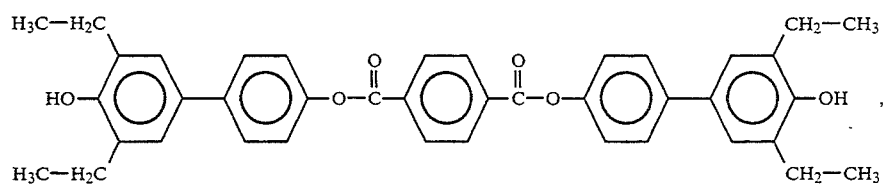

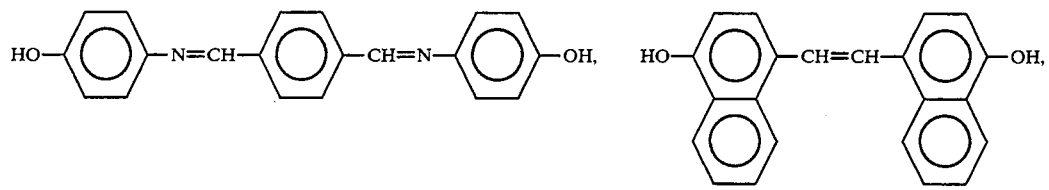
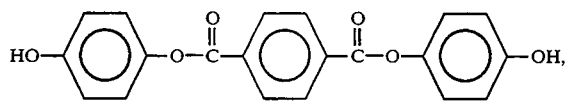
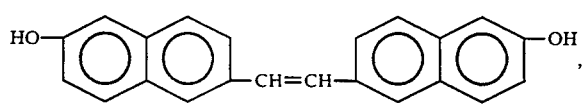
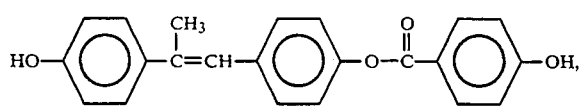
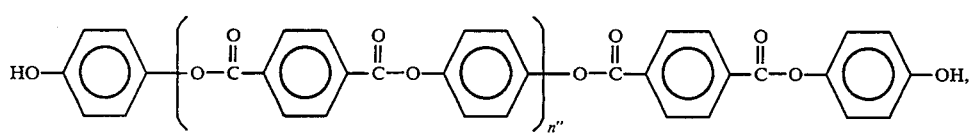
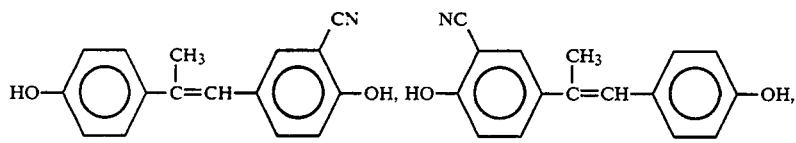
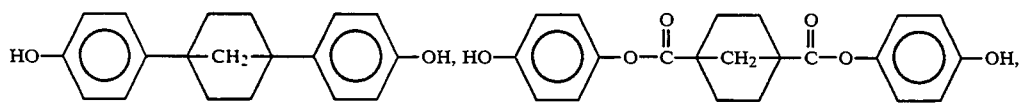
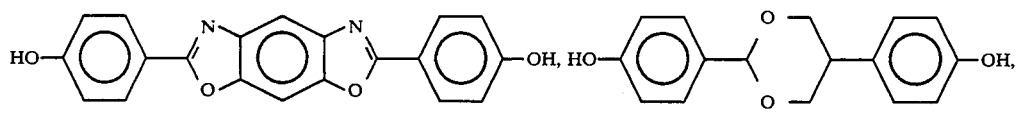
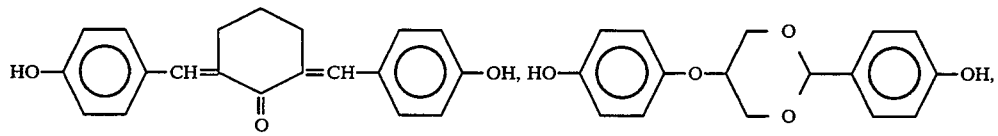
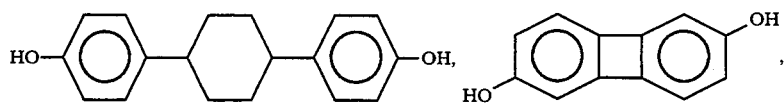
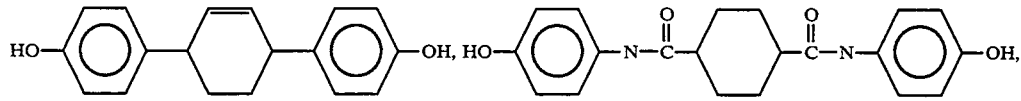

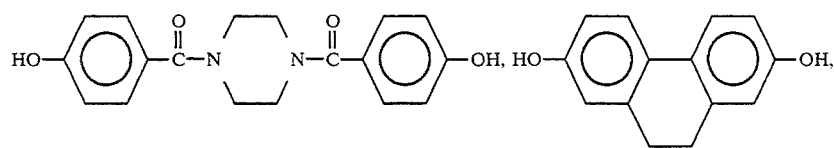
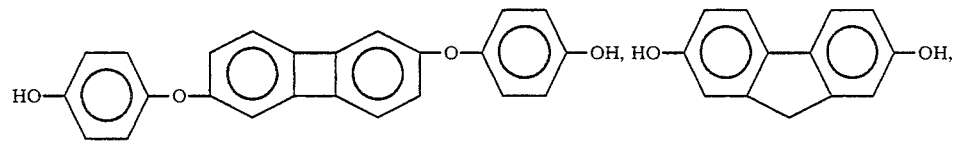
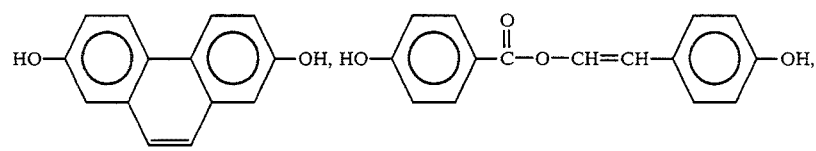
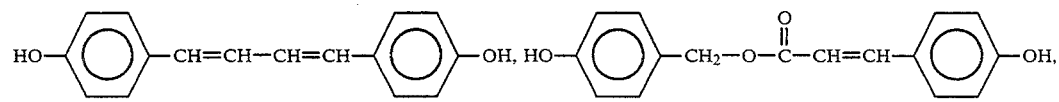
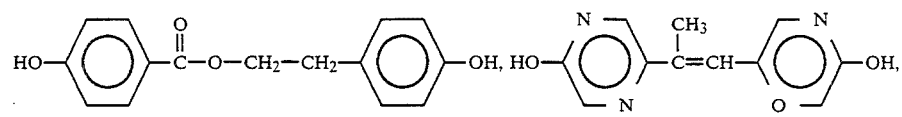
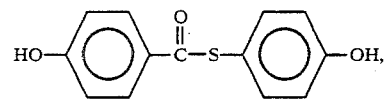
Particularly suitable polyamines are 4,4'-diaminostilbene, 4,4'-diamino-alpha-methylstilbene, 4,4'-diaminodiphenylacetylene, 4,4'-diamino-alpha-cyanostilbene, 4,4'-bis(4-aminophenoxy)diphenyl, 4,4'-diaminodiphenylazomethine, 4,4'-diamino-3,3'-dichlorobenzanilide, 4,4'-diamino-3,3'-dichloroazobenzene,
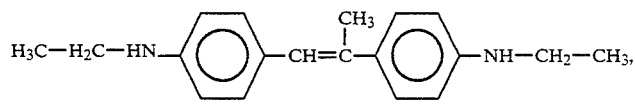
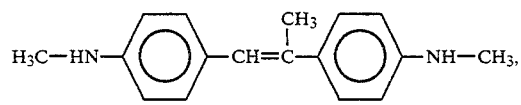
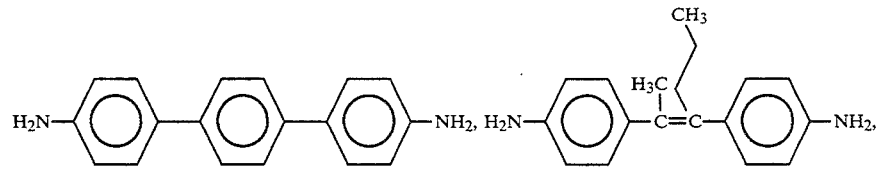
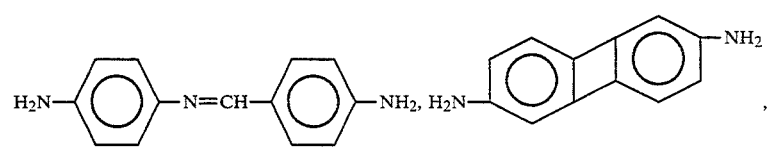

-continued

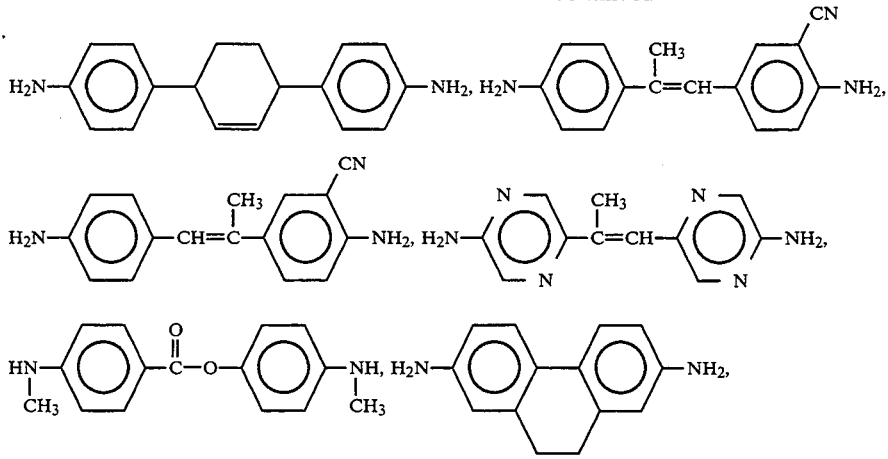

Particularly suitable aminophenols are 4-amino-4'-hydroxystilbene, 4-amino-4'-hydroxy-alpha-methylstilbene, 4-amino-4'-hydroxy-alpha-cyanostilbene, 4-amino-4'-hydroxybenzanilide, mixtures thereof and the like.

Suitable cyanogen halides include cyanogen chloride and cyanogen bromide. Alternately, the method of Martin and Bauer described in *Organic Synthesis*, volume 61, pages 35-68 (1983) published by John Wiley and Sons can be used to generate the required cyanogen halide in situ from sodium cyanide and a halogen such as chlorine or bromine.

Suitable base compounds include both inorganic bases and tertiary amines such as sodium hydroxide, potassium hydroxide, trimethylamine, triethylamine, mixtures thereof, and the like. Triethylamine is most preferred as the base.

Suitable solvents for the cyanation reaction include water, aliphatic ketones, chlorinated hydrocarbons, aliphatic and cycloaliphatic ethers and diethers, aromatic hydrocarbons, mixtures thereof and the like. Acetone methylethylketone, methylene chloride or chloroform are particularly suitable as the solvent.

CURING OF THE POLYCYANATES OR POLYCYANAMIDES CONTAINING ONE OR MORE RODLIKE MESOGENIC MOIETIES

The polycyanates or polycyanamides containing one or more rodlike mesogenic structure(s) are cured (thermoset) by heating from about 50° C. to about 400° C., preferrably by heating from 100° C. to 250° C., optionally in the presence of a suitable catalyst. Suitable catalysts include, for example, acids, bases, salts, nitrogen and phosphorus compounds, such as for example, Lewis acids such as AlCl$_3$, BF$_3$, FeCl$_3$, TiCl$_4$, ZnCl$_2$, SnCl$_4$; protonic acids such as HCl, H$_3$PO$_4$; aromatic hydroxy componds such as phenol, p-nitrophenol, pyrocatechol, dihydroxynaphthalene; sodium hydroxide, sodium methylate, sodium phenolate, trimethylamine, triethylamine, tributylamine, diazabicyclo[2.2.2]-octane, quinoline, isoquinoline, tetrahydroisoquinoline, tetraethylammonium chloride, pyridine-N-oxide, tributyl phosphine, zinc octoate, tin octoate, zinc naphthenate, cobalt naphthenate, cobalt octoate, cobalt acetylacetonate and the like. Also suitable as catalysts are the metal chelates such as, For example, the chelates of transition metals and bidentate or tridentate ligands, particularly the chelates of iron, cobalt, zinc, copper, manganese, zirconium, titanium, vanadium, aluminum and magnesium. These and other operable catalysts are disclosed in U.S. Pat. Nos. 3,694,410 and 4,094,852 which are incorporated herein by reference in their entirety. Cobalt naphthenate, cobalt octoate and cobalt acetylacetonate are most preferred as the catalysts. The quantity of catalyst used, if any, depends on the structure of the particular catalyst, the structure of the polycyanate or polycyanamide being cured, the cure temperature, the cure time, and the like. Generally, catalyst concentrations of from about 0.001 to about 2 percent by weight are preferred.

B-staging or prepolymerization of the compositions of the polycyanates or polycyanamides of the present invention can be accomplished by using lower temperatures and/or shorter curing times. Curing of the thus formed B-staged (prepolymerized) resin can then be accomplished at a later time or immediately following B-staging (prepolymerization) by increasing the temperature and/or curing time.

The cured (thermoset) products prepared from the polycyanates or polycyanamides containing rodlike mesogenic structure(s) possess the cyanate group homopolymerization structure

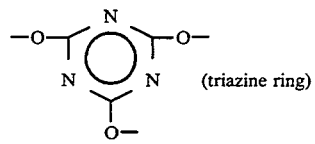 (triazine ring)

or the cyanamide group homopolymerization structure unless other functionalities are present in the polycyanate or polycyanamide that participate in the curing process. Such a case occurs in the curing of 4,4'-dicyanatobenzanilide where participation of the secondary amide hydrogen in the curing process leads to the formation of additional curing structure(s).

POLYCYANATES OR POLYCYANAMIDES WHICH DO NOT CONTAIN RODLIKE MESOGENIC MOIETIES AND WHICH CAN BE EMPLOYED IN THE CURABLE AND CURED COMPOSITIONS

Suitable polycyanates or polycyanamides which do not contain rodlike mesogenic structures and which can be employed to prepare the polymerizable mixtures of the present invention include, for example, those represented by the following Formulas IX, X, XI and XII

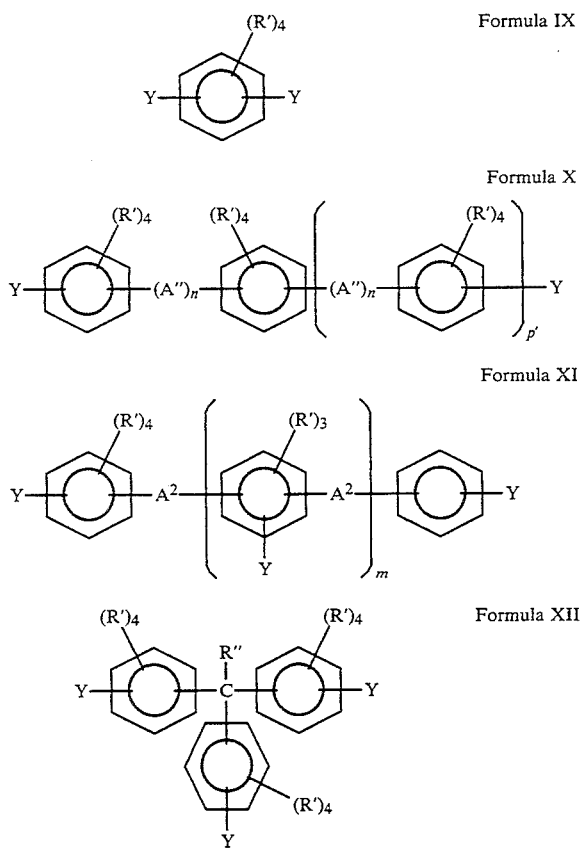

Formula IX

Formula X

Formula XI

Formula XII wherein Y, A″ and n are as hereinbefore defined; each $A^2$ is independently an alkylene group having from 1 to about 10, preferably from 1 to about 4 carbon atoms or a

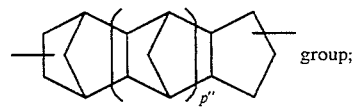 group;

each R′ is independently hydrogen, a hydrocarbyl or hydrocarbyloxy group having from 1 to about 10, preferably 1 to about 4 carbon atoms, a halogen, preferably chlorine or bromine, a phenyl group, a —O—C≡N group, or a —NR¹—C≡N group; each R″ is independently hydrogen, a hydrocarbyl or hydrocarbyloxy group having from 1 to about 10, preferably 1 to about 4 carbon atoms, a halogen, preferably chlorine or bromine, or a phenyl group; p′ has a value from zero to about 100, preferably from zero to about 30; p″ has a value of from zero to about 10, preferably from zero to 3 and m has a value of from about 0.001 to about 6, preferably from about 0.01 to about 3. The aromatic rings can also contain one or more heteroatoms selected from N, O, S and the like.

Suitable polycyanates or polycyanamides which do not contain rodlike mesogenic structures represented by Formulas IX, X, XI and XII include, for example, bisphenol A dicyanate, the dicyanates of 4,4′-dihydroxydiphenyl oxide, resorcinol, hydroquinone, 4,4′-thiodiphenol, 4,4′-sulfonyldiphenol, 3,3′,5,5′-tetrabromobisphenol A, 2,2′,6,6′-tetrabromobisphenol A, 2,2′-dihydroxy-diphenyl, 3,3′-dimethoxybisphenol A, 4,4′-dihydroxydiphenylcarbonate, dicyclopentadiene diphenol, 1,1-bis(p-hydroxyphenyl)cyclohexane, 4,4′-dihydroxybenzophenone, 4,4′-dihydroxydiphenyl methane, tricyclopentadiene diphenol, the tricyanate of tris(hydroxyphenyl)methane, the tetracyanate of 2,2′,4,4′-tetrahydroxydiphenyl methane, the polycyanate of a phenol formaldehyde condensation product (novolac), the polycyanate of a dicyclopentadiene and phenol condensation product, the dicyanamide of 4,4′-diaminodiphenyl methane, the cyanate/cyanamide of p-aminophenol, and the like.

The polycyanates or polycyanamides which do not contain rodlike mesogenic structures are prepared using the corresponding polyphenol, polyamine or aminophenol precursor and the previously described cyanation (cyanamidation) chemistry. As a specific process unique to the present invention, mixtures of one or more polyphenols, polyamines or aminophenols which do not contain rodlike mesogenic structures with one or more polyphenols, polyamines or aminophenols which contain one or more rodlike mesogenic structure(s) may be cyanated (cyanamidated) to provide a polymerizable mixture of the present invention.

EPOXY RESINS WHICH CAN BE EMPLOYED IN THE CURABLE AND CURED COMPOSITIONS

Suitable epoxy resins which can be employed to prepare the polymerizable mixtures of the present invention include materials having an average of more than one vicinal epoxide group per molecule, such as, for example, the epoxy resins represented by the following Formulas XIII, XIV, XV, XVI, XVII, XVIII, XIX, XX, XXI, XXII

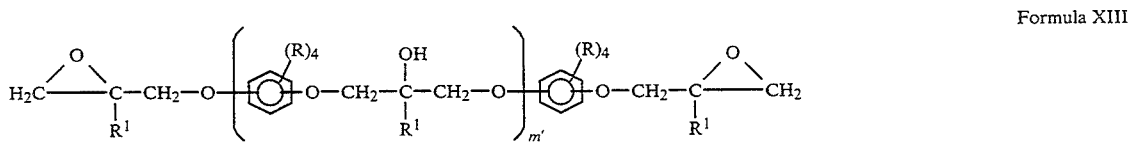

Formula XIII

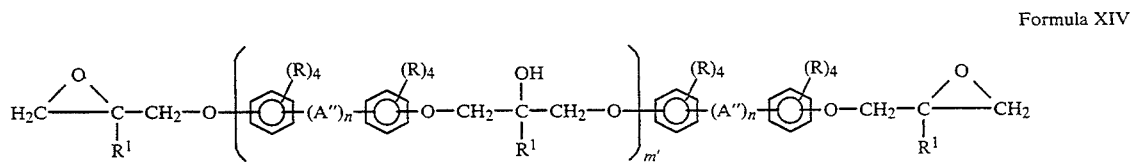

Formula XIV

Formula XV
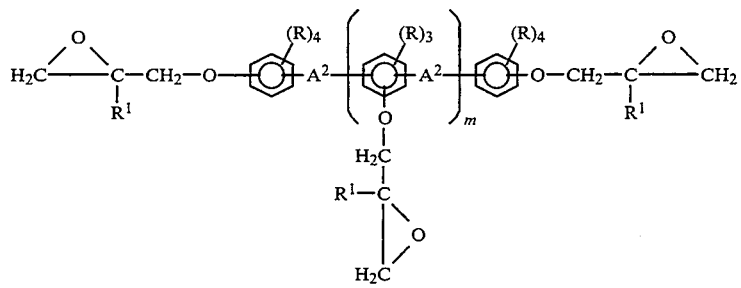
Formula XVI
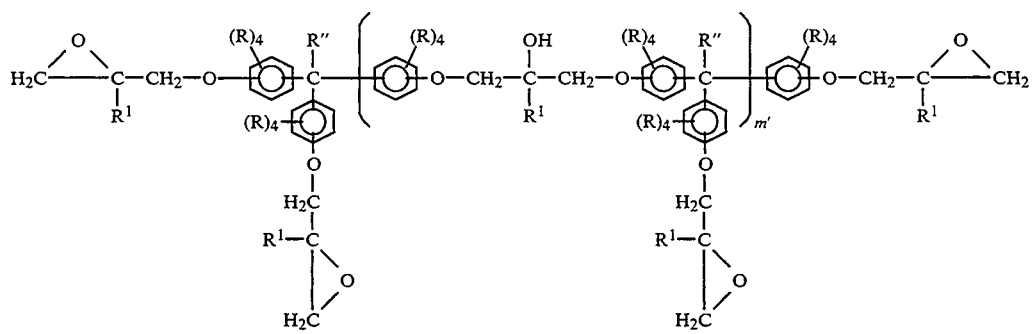
Formula XVII
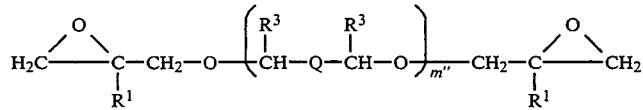
Formula XVIII
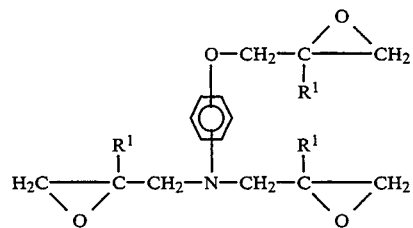
Formula XIX
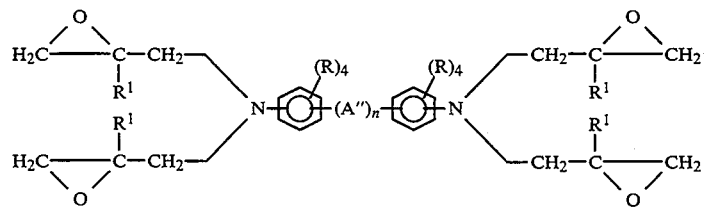
Formula XX
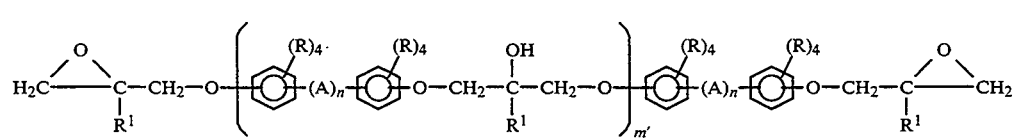
Formula XXI
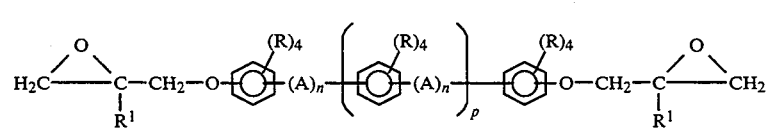

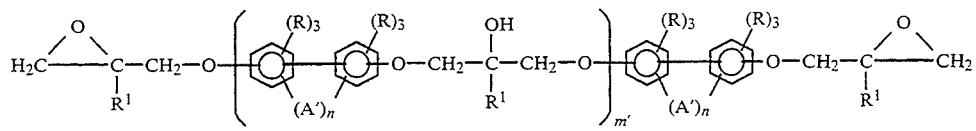

Formula XXII wherein A, $A^2$, A', A'', R, $R^1$, R'', m, p and n are as hereinbefore defined; each $R^3$ is independently hydrogen, or a hydrocarbyl or halohydrocarbyl group having from 1 to about 6, preferably 1 to about 2 carbon atoms; Q is a direct bond, —$CH_2$—S—$CH_2$—, —$(CH_2)_{n'''}$—, or

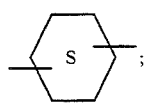

m' has a value of from zero to about 30, preferably from about zero to about 5; m'' has a value from 1 to about 10, preferably from about 1 to about 4 and n'' has an average value from about 1 to about 10. The aromatic rings can also contain one or more heteroatoms selected from N, O, S and the like.

Particularly suitable epoxy resins represented by Formulas XIII, XIV, XV, XVI, XVII, XVIII, XIX, XX, XXI and XXII are the diglycidyl ethers of resorcinol, hydroquinone, dihydroxydiphenyl methane, bisphenol A, 3,3',5,5'-tetrabromobisphenol A, 4,4'-sulfonyldiphenol, 4,4'-thiodiphenol, 4,4'-dihydroxydiphenyl oxide, 4,4'-dihydroxybenzophenone, 2,2'-dihydroxydiphenyl, dicyclopentadiene diphenol, tricyclopentadiene diphenol, 4,4'-dihydroxydiphenyl, 4,4'-dihydroxystilbene, 4,4'-dihydroxy-alpha-methylstilbene, 4,4'-dihydroxy-alpha-cyanostilbene, 4,4'-dihydroxychalcone, 4,4'-dihydroxydiphenylacetylene, 4,4'-dihydroxydiphenylazomethine, 4,4'-dihydroxyazobenzene, 4,4'-bis(4-hydroxyphenoxy)diphenyl, 4,4'-dihydroxybenzanilide, ethylene glycol, thiodiglycol, diethylene glycol, dipropylene glycol, polypropylene glycol, polyethylene glycol, 1,4-cyclohexanediol, dibutylene glycol, the advancement reaction product of the diglycidyl ether of bisphenol A and bisphenol A, the advancement reaction product of the diglycidyl ether of 4,4'-dihydroxy-alpha-methylstilbene and 4,4'-dihydroxy-alpha-methylstilbene, the triepoxide of p-aminophenol, the tetraepoxide of 4,4'-diaminodiphenyl methane, the triglycidyl ether of tris(hydroxyphenyl)methane, the tetraglycidyl ether of 2,2',4,4'-tetrahydroxydiphenyl methane, the polyglycidyl ether of a phenolformaldehyde condensation product (novolac), the polyglycidyl ether of a dicyclopentadiene or oligomer thereof and phenol or halogen or alkyl substituted phenol condensation product and the like.

The aforementioned epoxy resins can be prepared by reaction of a polyphenol (polyamine, aminophenol, polyalkylene glycol) with an epihalohydrin and a basic acting material. Said reaction generally involves two distinct steps: coupling reaction of the epihalohydrin and polyphenol to provide a halohydrin intermediate and dehydrohalogenation reaction of the halohydrin intermediate to provide the glycidyl ether product. Suitable catalysts and reaction conditions for preparing epoxy resins are described in the *Handbook of Epoxy Resins* by Lee and Neville, McGraw-Hill (1967) which is incorporated herein by reference.

POLYMALEIMIDES FOR USE IN THE CURABLE AND CURED COMPOSITIONS

Suitable polymaleimides which can be employed to prepare the polymerizable mixtures of the present invention include, for example, those represented by the Formulas

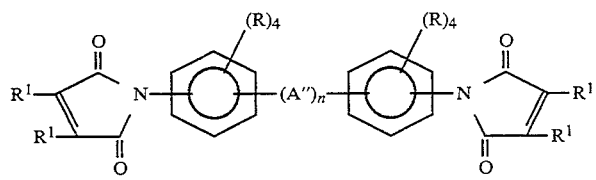

Formula XXIII

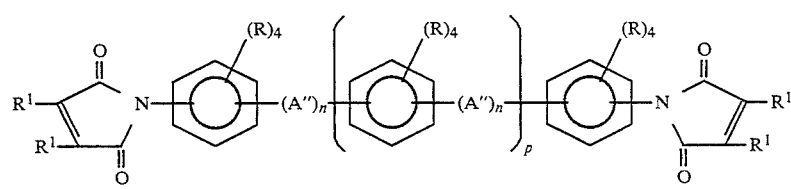

Formula XXIV

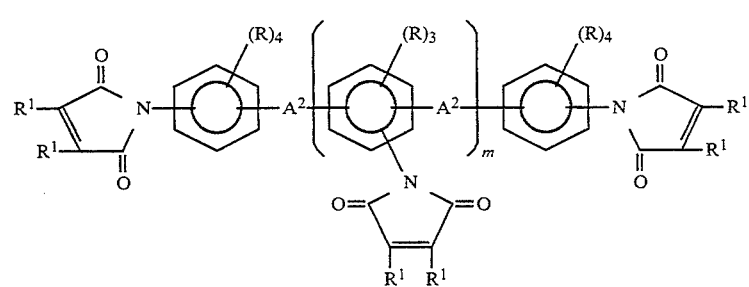

Formula XXV

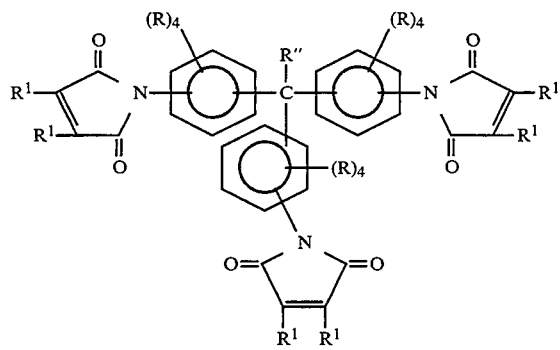

Formula XXVI

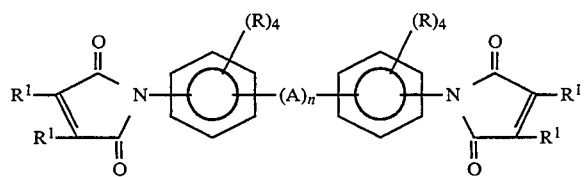

Formula XXVII

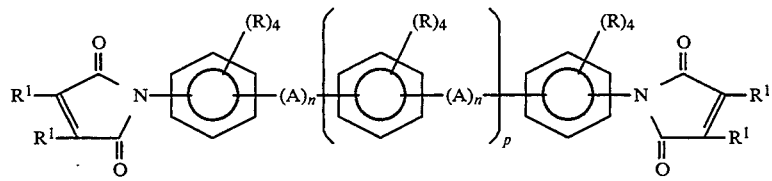

Formula XXVIII

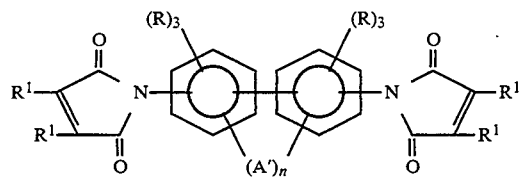

Formula XXVIX

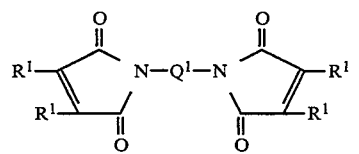

Formula XXX wherein A, $A^2$, A', A", R, $R^1$, R", m, n and p are as hereinbefore defined and $Q^1$ is a divalent hydrocarbyl group having from 2 to about 12 carbon atoms and may be linear or branched aliphatic, cycloaliphatic or polycycloaliphatic. The aromatic rings can also contain one or more heteroatoms selected from N, O, S and the like.

Particularly suitable polymaleimides represented by Formulas XXIII, XXIV, XXV, XXVI, XXVII, XXVIII, XXIX and XXX are N,N'-ethylenebismaleimide, N,N'-ethylenebis(2-methylmaleimide), N,N'-hexamethylenebismaleimide, N,N'-(oxydi-p-phenylene)bismaleimide, N,N'-(methylenedi-p-phenylene)maleimide, N,N'-(methylenedi-p-phenylene)bis(2-methylmaleimide), N,N'-(thio-di-p-phenylene)bismaleimide, N,N'-(sulfonyldi-m-phenylene)bismaleimide, N,N'-(isopropylidenedi-p-phenylene)bismaleimide, polymethylene polyphenylene polymaleimides, the bismaleimide of 4,4'-diaminostilbene, the bismaleimide of 4,4'-diaminobenzanilide and the like.

The polymaleimides can be prepared by reacting a stoichiometric quantity of a maleic anhydride per amine group with a polyamine in the presence of a suitable solvent, such as, for example, aromatic hydrocarbons, chlorinated hydrocarbons or N,N-dimethylformamide. The polymaleamic acid resulting from reaction of a maleic an hydride and a polyamine may be isolated and dehydrated to the desired polymaleimide. Alternately, the reaction may be performed in a single continous step. Detailed procedures for preparing polymaleimides can be found in U.S. Pat. Nos. 2,444,536; 2,462,835, and *Journal of Polymer Science: Part A: Polymer Chemistry*, Vol. 27, pages 375–388 (1989) which are incorporated herein by reference.

POLYAMINES SUITABLE FOR USE IN THE CURABLE AND CURED COMPOSITIONS

Suitable polyamines which can be employed to prepare the polymerizable mixtures of the present invention, include those containing one or more of the rodlike mesogenic structure(s) already described herein, as well as any of the other known polyamines which do not contain rodlike mesogenic structures. Typical representatives of said polyamines free of rodlike mesogenic structures include 1,4-diamino-butane, 1,6-hexanediamine, 1,12-diaminododecane, 2-methyl-4-ethyl-1,8-diaminooctane, 1,4-diamino-cyclohexane, 4,4'- diaminodiphenyl methane, 1,4-diaminobenzene, tris-(aminophenyl)methane, anilineformaldehyde condensation products and the like.

POLYPHENOLS SUITABLE FOR USE IN THE CURABLE AND CURED COMPOSITIONS

Suitable polyphenols which can be employed to prepare the polymerizable mixtures of the present invention, include those containing one or more of the rodlike mesogenic structure(s) already described herein as well as any of the other known polyphenols which do not contain rodlike mesogenic structures. Typical representatives of said polyphenols free of mesogenic or rodlike structures include resorcinol, 4,4′-sulfonyldiphenol, 4,4′-dihydroxydiphenyl oxide, tris(hydroxyphenyl)methane, phenolformaldehyde condensation products and the like.

POLYMERIZABLE UNSATURATED MONOMERS SUITABLE FOR USE IN THE CURABLE AND CURED COMPOSITIONS

Suitable compounds containing one or more polymerizable ethylenically unsaturated group(s) which can be employed to prepare the polymerizable mixtures of the present invention include both those containing one or more rodlike mesogenic structure(s) and those free of said structures.

Suitable polymerizable ethylenically unsaturated monomers containing one or more rodlike mesogenic moieties are cataloged by Alexandre Blumstein in *Liquid Crystalline Order in Polymers*, published by Academic Press, New York (1978) on pages 105–140; *Mesomorphic Order in Polymers and Polymerization in Liquid Crystalline Media* published by American Chemical Society (ACS Symposium Series 74), Washington, D.C. (1978) on pages 56–70; and N. A. Plate and V. P. Shibaev in *Comb-Shaped Polymers and Liquid Crystals* published by Plenum Press, New York (1987) on pages 1–415, V. Percec, et. al., *Polymer Bulletin*, 17, pages 347–352 (1987); R. Duran and P. Gramain, *Makromol. Chem.*, 188, pages 2001–2009 (1987); A. M. Mousa, et. al., *Polymer Bulletin*, 6, pages 485–492 (1982); H. Finkelmann, et. al., *Makromol. Chem.*, 179, pages 829–832 (1978); M. Portugall, et. al., *Makromol. Chem.*, 183, pages 2311–2321 (1982) and U.S. Pat. Nos. 4,637,896 and 4,614,619, all of which are incorporated herein by reference. Suitable polymerizable ethylenically unsaturated monomers containing one or more rodlike mesogenic moieties per molecule are represented by the Formulas XXXI or XXXII:

M—$Q^2$                                          Formula XXXI

M—$(Q^3)_n$—$R^4$—$Q^2$               Formula XXXII wherein n and $R^1$ are as hereinbefore defined, M is a group containing two or more aromatic rings bridged by a rigid central linkage, $R^4$ is a divalent hydrocarbon group having from one to about 12 carbon atoms and may be linear, branched, cyclic, aromatic or a combination thereof and may be substituted with one or more inert groups, such as, for example, a methoxy group, or may contain one or more inert heteroatom containing linkages, such as, for example, an ether linkage; $Q^3$ is —O—, —$NR^1$—, —S—, —O—CO—, —CO—O—, —$NR^1$—CO—, —CO—$NR^1$—, —CO—, —O— CO—O—, —S—CO—, —CO—S—, —$NR^1$—CO—O—, —O—CO—$NR^1$—, —$NR^1$—CO—$NR^1$—, and $Q^2$ is a polymerizable ethylenically unsaturated group. As a class, these monomers generally contain a —CH=$CH_2$, allyl, methallyl, propenyl, isopropenyl, acrylate or methacrylate group as the polymerizable ethylenically unsaturated group and a linear divalent aliphatic, aliphatic ether, aliphatic polyether, aliphatic thioether or cycloaliphatic flexible spacer connecting the polymerizable ethylenically unsaturated group and the rodlike mesogenic group(s) through a heteroatom linkage. Typical rodlike mesogenic groups include those wherein two or more aromatic rings are bridged by a rigid central linkage wherein said rigid central linkage is required to bridge the aromatic rings to provide at least about 80 percent para substitution. The aromatic rings can be inertly substituted, however, unsubstituted aromatic rings which maximize the molecular aspect ratio are preferred. Also preferred is a single inert substituent in the para position on the ring not connected to the polymerizable ethylenically unsaturated group (either directly or via a flexible spacer). This type of substituent can be used to enhance the molecular aspect ratio. Typical of these inert substituents are $CH_3O$—, Cl—, $NO_2$—, —C≡N and the like. The aromatic rings can also contain one or more heteroatoms selected from N, O, S and the like. Typical rigid central linkage groups for bridging the aromatic rings include, for example, a direct bond, —$CR^1$=$CR^1$—, —C≡C—, —N=N—, —$CR^1$=N—, —$CR^1$=N—$NR^1$=$CR^1$—, —$CR^1$=$CR^1$—CO—, —O—CO—, —$NR^1$—CO—, —CO—O—, —CO—$NR^1$—, —CO—$CR^1$=$CR^1$13 , —$CR^1$=$CR^1$—O—CO—$(CH_2)_{n'}$—, —N=$CR^1$—, —$(CH_2)_{n'}$—CO—O—$CR^1$=$CR^1$, —$CR^1$=$CR^1$—O—CO—, —CO—O—$CR^1$=$CR^1$—, —CO—O—N=$CR^1$—, —$CR^1$=N—O—CO—, —CO—S—, —$CR^1$=$CR^1$—CO—O—, —O—CO—$CR^1$=$CR^1$—, —$CR^1$=$CR^1$—CO—O—$(CH_2)_{n'}$—, —S—CO—, —$(CH_2)_{n'}$—O—CO—$CR^1$=$CR^1$—, —$CHR^1$—$CHR^1$—CO—O—, —O—CO—$CHR^1$—$CHR^1$—, —C≡C—C≡C—, —$CR^1$=$CR^1$—$CR^1$=$CR^1$—, —CO—$NR^1$—$NR^1$—CO—,

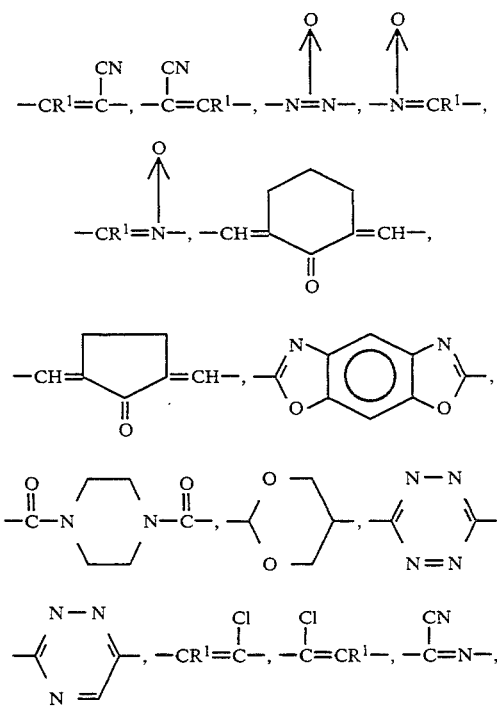

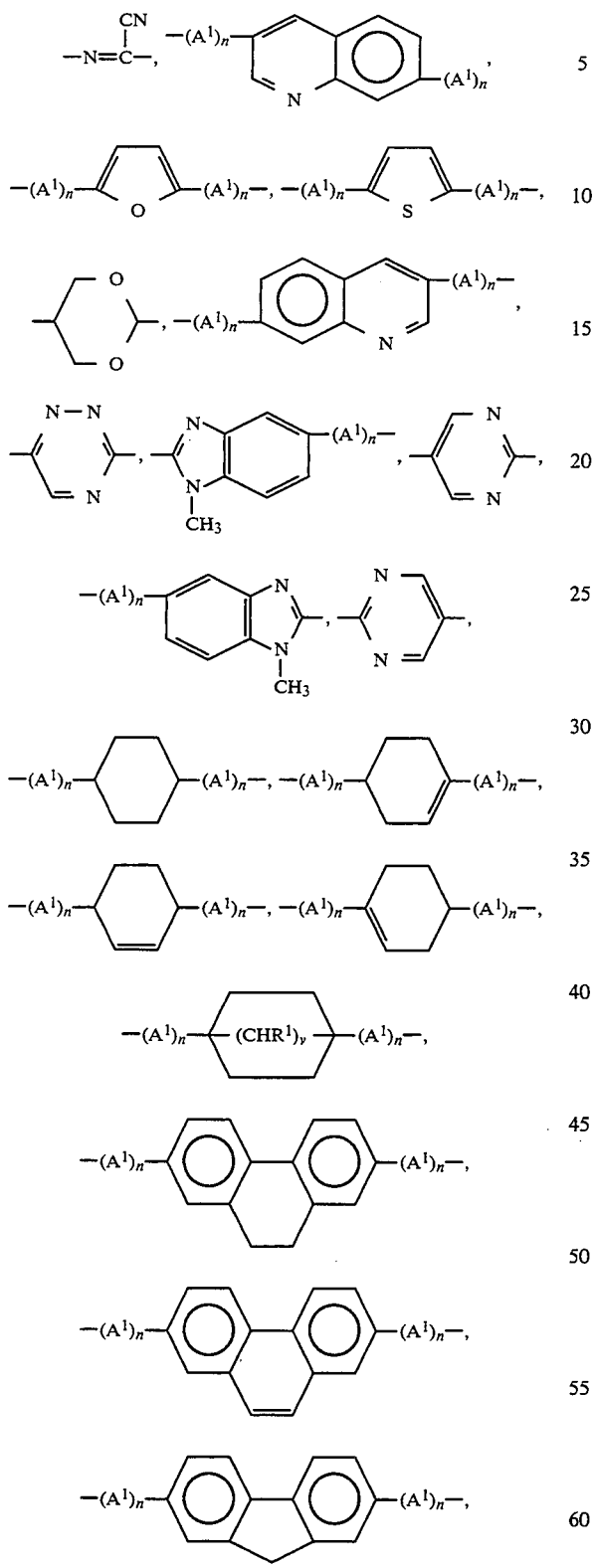

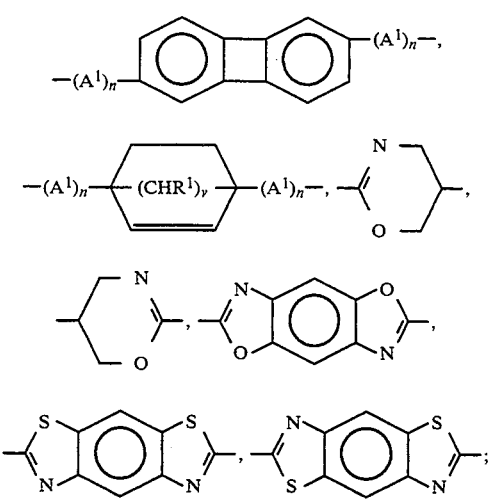

and the like; wherein $R^1$, $A^1$, v, n and n' are as hereinbefore defined. As is well known in the prior art, all or a part of the aromatic rings can be replaced with other promesogenic structures, such as, for example, the trans-cyclohexane ring or a cholesterol group Additionally, it is has been demonstrated in the prior art that efficacious rodlike mesogen containing polymerizable ethylenically unsaturated monomers can be prepared with omission of the flexible spacer between the polymerizable ethylenically unsaturated group and the rodlike mesogenic group(s).

Generally, the ethylenically unsaturated monomers containing —CH=CH$_2$, acrylate, allyl, methallyl, propenyl, isopropenyl or methacrylate as the polymerizable vinyl group and a linear divalent hydrocarbon group connecting the vinyl group and the rodlike mesogenic group through heteroatom containing functional groups between the hydrocarbon spacer and the mesogenic group are most preferred. Thus, a rodlike mesogenic group ether linked to a —CH$_2$—CH$_2$— which is in turn linked to provide a methacrylate ester, that is,

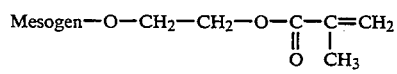

or a rodlike mesogenic group linked to a vinyl group, that is,

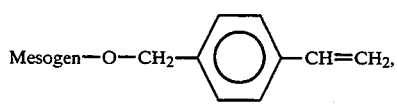

are examples of those species preferred as the ethylenically unsaturated monomer containing one or more rodlike mesogenic moieties.

Particularly suitable ethylenically unsaturated monomers containing a rodlike mesogenic moiety include, for example,

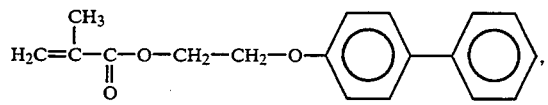
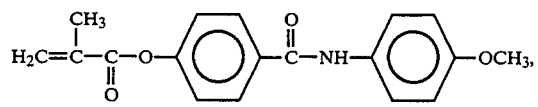

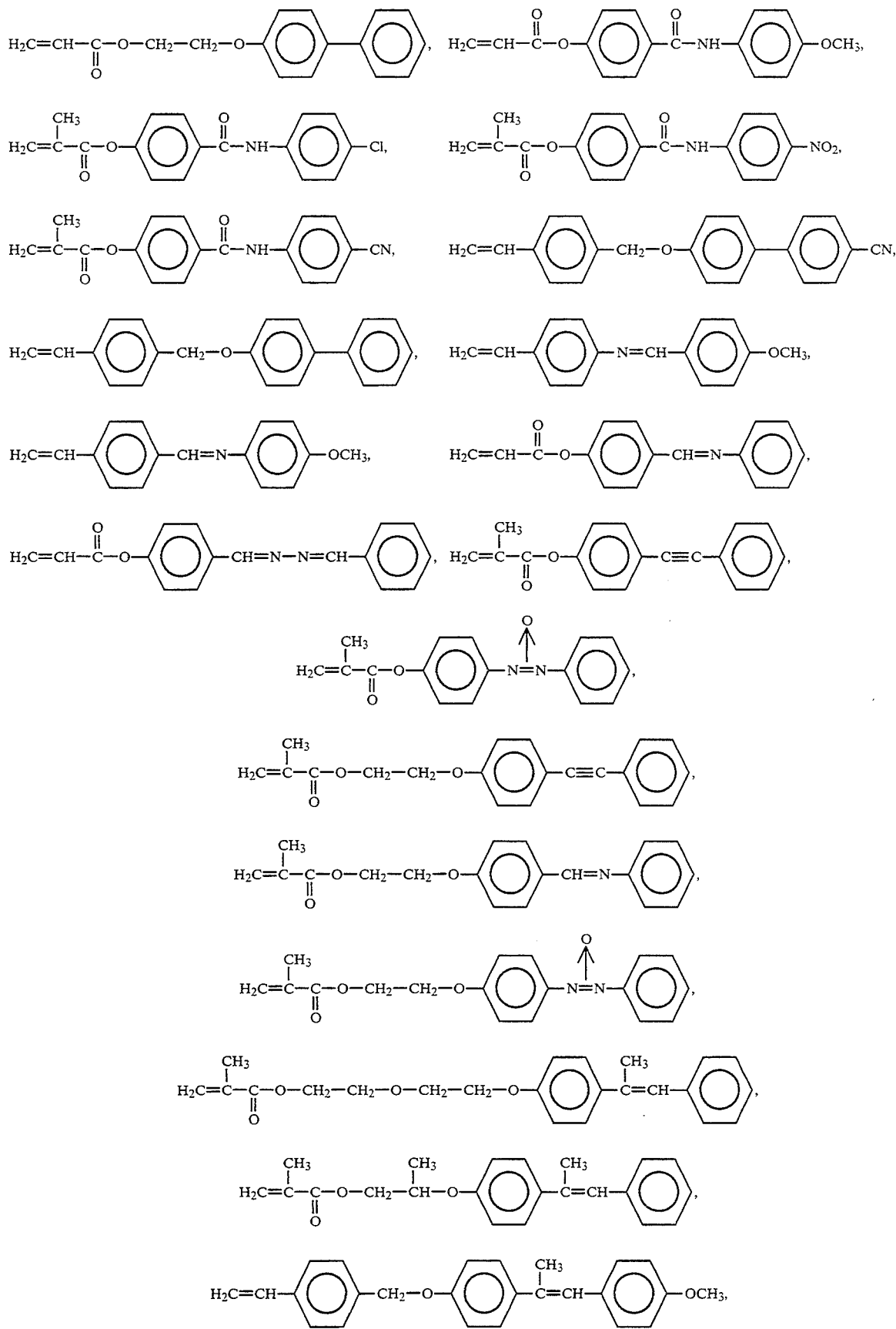

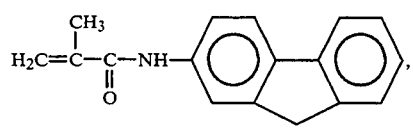
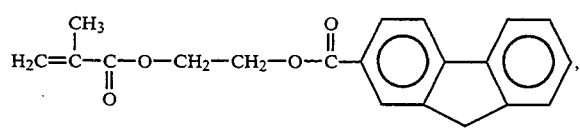
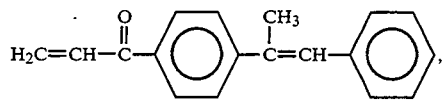
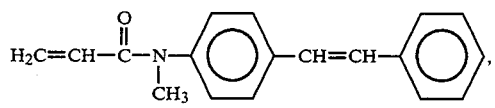
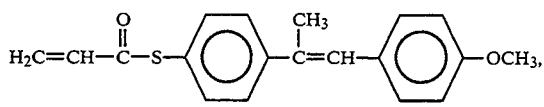
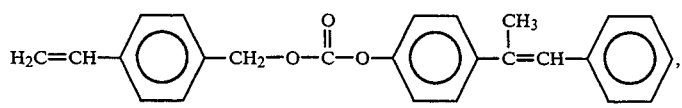
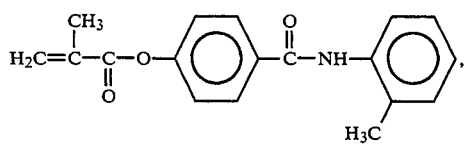
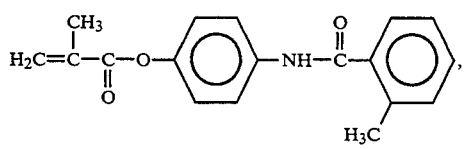
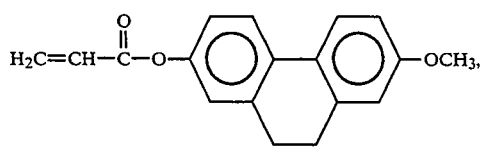
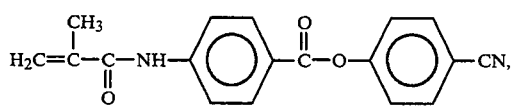
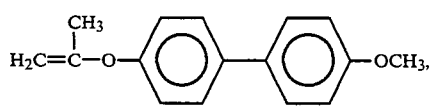
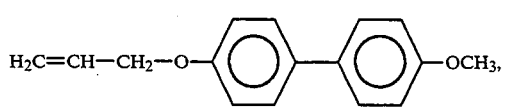
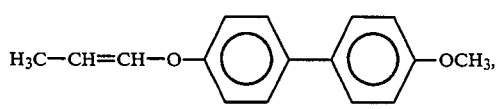
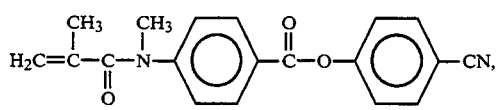
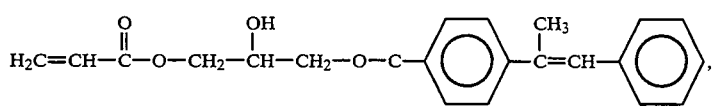
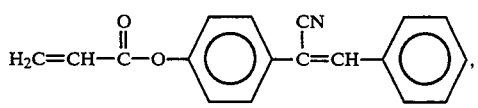
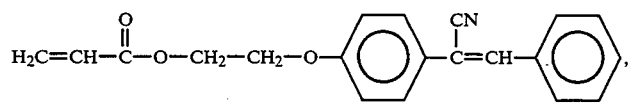
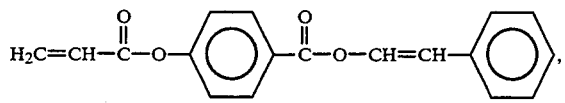
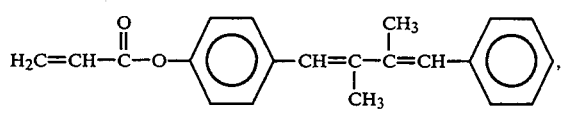

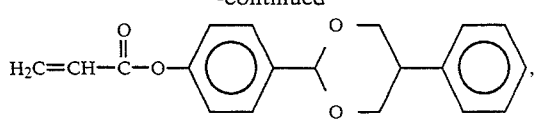

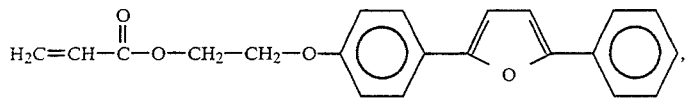

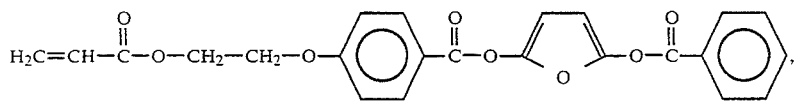

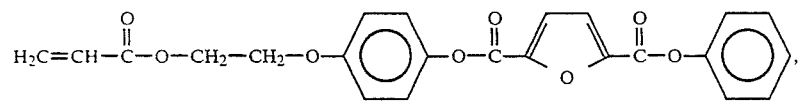

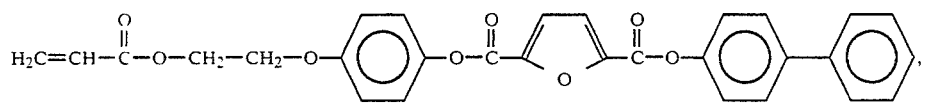

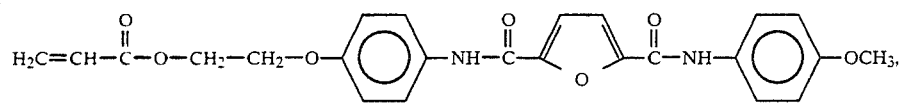

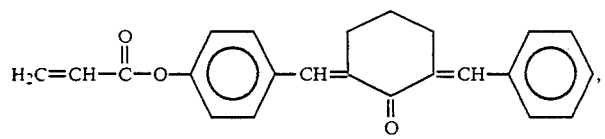

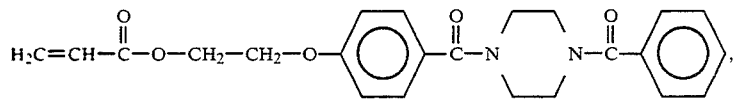

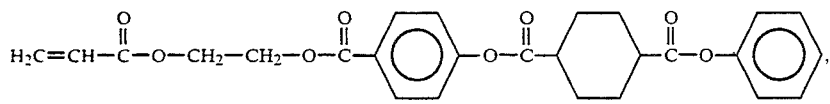

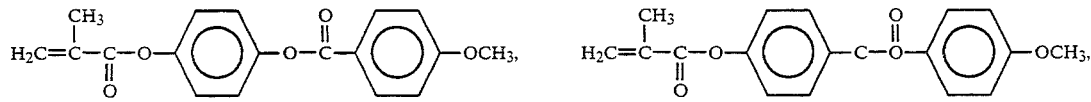

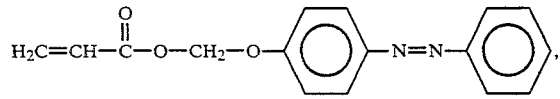

any combination thereof and the like.

Suitable polymerizable ethylenically unsaturated monomers which do not contain rodlike mesogenic structures can be selected from the many known classes of polymerizable vinyl monomers. Suitable such monomers include, for example, the vinyl aromatic compounds represented by the following Formula XXXIII

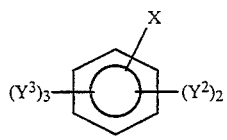

Formula XXXIII wherein each $R^1$ is as hereinbefore defined. $Y^2$ is independently hydrogen, a hydrocarbyl or hydrocarbyloxy group having from 1 to about 5 carbon atoms, a vinyl group, an allyl group, a methallyl group, a propenyl group, a isopropenyl group, a nitro group, a nitrile group, a halogen, such as chlorine or bromine or fluorine, or a —CO—R$^1$ group; each Y$^3$ is independently hydrogen, a hydrocarbyl or hydrocarbyloxy group having from 1 to about 5 carbon atoms, or a halogen, such as chlorine or bromine or fluorine and X is

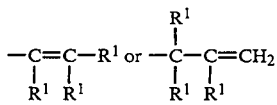

or the acrylate or methacrylate compounds represented by the following Formula XXXIV

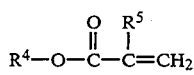

Formula XXXIV wherein R$^4$ is a hydrocarbyl group having from 2 to about 25 carbon atoms and may be branched, cyclic, polycyclic, saturated or unsaturated and R$^5$ is hydrogen or a methyl group.

Typical polymerizable unsaturated monomers represented by Formula XXXIII include, for example, styrene, alpha-methylstyrene, o-, m-, p-chlorostyrene; o-, m-, p-bromostyrene; o-, m-, p-tert-butylstyrene; o-, m-, p-methylstyrene, o-, m-, p-methoxystyrene; divinylbenzenes, trivinylbenzenes, o-, m-, p-isopropenylstyrene; o-, m-, p-allylstyrene; o-, m-, p-methallylstyrene; allylbenzene, methallylbenzene, diallylbenzenes and the like.

Typical acrylate (methacrylate) esters represented by Formula XXXIV include, for example, ethyl acrylate, n-butyl acrylate, n-butyl methacrylate, sec-butyl acrylate, 2-ethylhexyl acrylate, 2-ethylhexyl methacrylate, n-dodecyl acrylate, cyclohexyl acrylate, methylcyclohexyl acrylate, norbornyl acrylate, dicyclopentadiene acrylate, methyldicyclopentadiene acrylate and the like.

Other suitable monomers include the acidic monomers, such as acrylic and methacrylic acid; the amide monomers, such as acrylamide and N-methylacrylamide; the allyl monomers, such as diallylphthalate, triallylisocyanurate, diallylmaleate and dimethallylfumarate; the vinyl halides, such as vinyl chloride and vinyl bromide; the vinyl esters, such as vinyl acetate; the vinyl di and polycyclic aromatics, such as vinyl naphthalene; the vinyl nitriles, such as acrylonitrile; and the hydroxyalkyl acrylates and methacrylates, such as 2-hydroxyethyl acrylate.

COMPOUNDS CONTAINING BOTH A CYANATE OR CYANAMIDE GROUP AND A POLYMERIZABLE ETHYLENICALLY UNSATURATED GROUP FOR USE IN THE CURABLE AND CURED COMPOSITIONS

Suitable compounds which contain both a cyanate or cyanamide group and a polymerizable ethylenically unsaturated group in the same molecule that can be used to prepare the polymerizable mixtures of the present invention include, for example, those represented by the following Formula XXXV

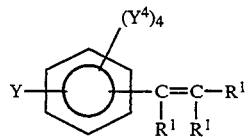

Formula XXXV wherein each Y and R$^1$ are as hereinbefore defined. Y$^4$ is independently hydrogen, a hydrocarbyl or hydrocarbyloxy group having from 1 to about 12 carbon atoms, a nitro group, a nitrile group, a halogen, such as chlorine or bromine or fluorine, or a —CO—R$^1$ group; or a compound represented by the following Formula XXXVI

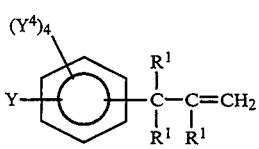

Formula XXXVI wherein each Y, Y$^4$ and R$^1$ are as hereinbefore defined.

Suitable compounds which contain a cyanate or cyanamide group and a polymerizable ethylenically unsaturated group in the same molecule represented by Formulas XXXV and XXXVI include, for example, o-, m-, p-isopropenylphenyl cyanate; o-, m-, p-vinylphenyl cyanate; methyl-p-isopropenylphenyl cyanates; 3-chloro-4-isopropenylphenyl cyanate; o-, m-, p-propenylphenyl cyanate; o-, m-, p-allylphenyl cyanate; o-, m-, p-methallylphenyl cyanate and the like. Some of the alkenylphenol precursors to the alkenylphenyl cyanates represented by Formula XXXV, notably the vinylphenols, have a tendency to dimerize or oligomerize thus leading to poly(alkenylphenyl)cyanates. It is most preferred that the alkenylphenyl cyanate be substantially free of dimeric and/or oligomeric components, although it is operable to use an alkenylphenyl cyanate containing substantial (up to 90 percent by weight) dimeric and/or oligomeric components. A specific preparation of p-isopropenylphenyl cyanate is taught in Example 1 of U.S. Pat. No. 4,559,399 which is incorporated herein by reference.

COMPOUNDS CONTAINING BOTH A 1,2-EPOXIDE GROUP AND A POLYMERIZABLE ETHYLENICALLY UNSATURATED GROUP FOR USE IN THE CURABLE AND CURED COMPOSITIONS

Suitable compounds which contain both a 1,2-epoxide group and a polymerizable ethylenically unsaturated group in the same molecule that can be used to prepare the polymerizable mixtures of the present invention include, for example, those represented by the following Formulas XXXVII or XXXVIII

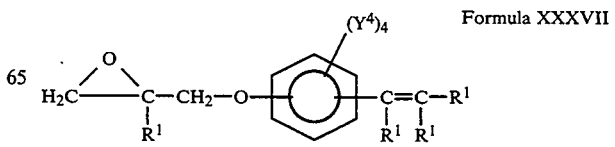

Formula XXXVII

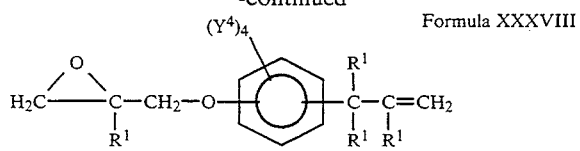

Formula XXXVIII wherein each $Y^4$ and $R^1$ are as hereinbefore defined.

Suitable compounds which contain a 1,2-epoxide group and a polymerizable ethylenically unsaturated group in the same molecule represented by Formulas XXXVII and XXXVIII include, for example, o-, m-, p-isopropenylphenyl glycidyl ether; o-, m-, p-vinylphenyl glycidyl ether; methyl-p-isopropenylphenyl glycidyl ethers; 3-chloro-4-isopropenylphenyl glycidyl ether; o-, m-, p-propenylphenyl glycidyl ether; o-, m-, p-allylphenyl glycidyl ether; o-, m-, p-methallylphenyl glycidyl ether and the like. Some of the alkenylphenol precursors to the alkenylphenyl glycidyl ethers represented by Formula XXXVII, notably the vinylphenols, have a tendency to dimerize or oligomerize thus leading to poly(alkenylphenyl)glycidyl ethers. It is most preferred that the alkenylphenyl glycidyl ether be substantially free of dimeric and/or oligomeric components, although it is operable to use an alkenylphenyl glycidyl ether containing substantial (up to 90 percent by weight) dimeric and/or oligomeric components. The compounds which contain a 1,2-epoxide group and a polymerizable ethylenically unsaturated group in the same molecule are prepared using the corresponding phenol containing a polymerizable ethylenically unsaturated group and the hereinbefore described chemistry used in the preparation of epoxy resins.

COMPOUNDS CONTAINING BOTH A MALEIMIDE GROUP AND A CYANATE GROUP SUITABLE FOR USE IN THE CURABLE AND CURED COMPOSITIONS

Suitable compounds which contain both a maleimide group and a cyanate group in the same molecule that can be used to prepare the polymerizable mixtures of the present invention include, for example, those represented by the following Formulas XXXIX, XXXX or XXXXI

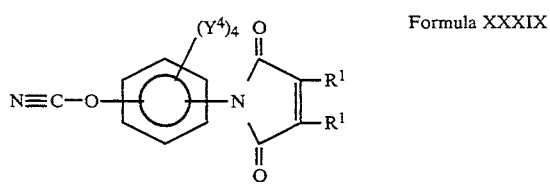

Formula XXXIX

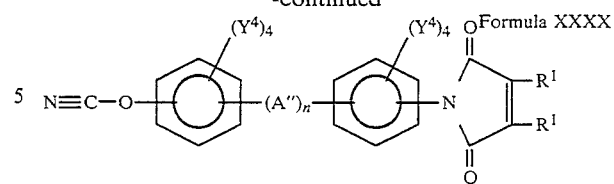

Formula XXXX

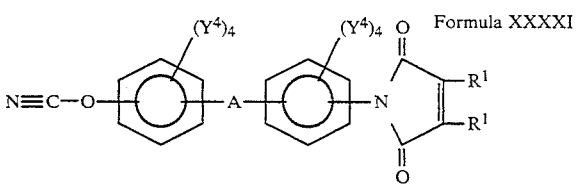

Formula XXXXI wherein each $Y^4$, $R^1$, A, A'' and n are as hereinbefore defined.

Suitable compounds which contain a maleimide group and a cyanate group in the same molecule represented by Formulas XXXIX, XXXX and XXXXI include, for example, 4-(1-(3-(2,5-dihydro-2,5-dioxo-1H-pyrrol-1-yl)phenyl)-1-methylethyl)phenyl cyanate; 4-(1-(4-(2,5-dihydro-2,5-dioxo-1H -pyrrol-1-yl)phenyl)-1-methylethyl)phenyl cyanate; 4-(1-(4-(2,5-dihydro-2,5-dioxo-1H-pyrrol-1-yl)phenyl)ethyl)phenyl cyanate; 4-(4-(2,5-dihydro-2,5-dioxo-1H-pyrrol-1-yl)phenoxy)phenyl cyanate; 4-((4-(2,5-dihydro-2,5-dioxo-1H-pyrrol-1-yl)phenyl)thio)phenyl cyanate; 4-(4-(2,5-dihydro-2,5-dioxo-1H-pyrrol-1-yl)benzoyl)phenyl cyanate; 4-((4-(2,5-dihydro-2,5-dioxo-1H-pyrrol-1-yl)phenyl)sulfonyl)phenyl cyanate; 4-(1-(4-(2,5-dihydro-3-methyl-2,5-dioxo-1H-pyrrol-1-yl)phenyl)-1-methylethyl)phenyl cyanate; 2,6-dibromo-4-(1-(3,5-dibromo-4-(2,5-dihydro-2,5-dioxo-1H-pyrrol-1-yl)phenyl)-1-methylethyl)-phenylcyanate; 4-(2,5-dihydro-2,5-dioxo-1H-pyrrol-1-yl)phenyl cyanate; 3-(2,5-dihydro-2,5-dioxo-1H-pyrrol-1-yl)phenyl cyanate and the like. Preparation of compounds which contain a maleimide group and a cyanate group in the same molecule is taught in U.S. Pat. No. 4,683,276 which is incorporated herein by reference.

COMPOUNDS CONTAINING ONE CYANATE OR CYANAMIDE GROUP PER MOLECULE AND ONE OR MORE RODLIKE MESOGENIC MOIETIES WHICH CAN BE EMPLOYED IN THE CURABLE AND CURED COMPOSITIONS

Suitable compounds which contain one or more rodlike mesogenic structure(s) and an average of one cyanate or cyanamide group per molecule that can be used to prepare the polymerizable mixtures of the present invention include, for example, those represented by the following Formulas XXXXII, XXXXIII, XXXXIV, or XXXXV

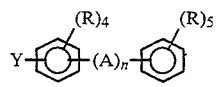

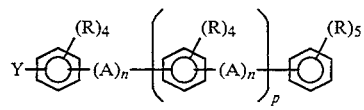

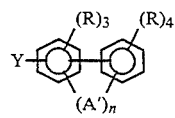

Formula XXXXV

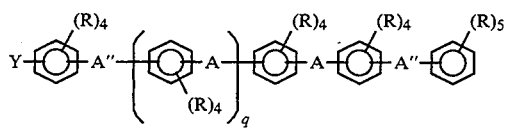

wherein at least 80 percent of the —A— linkages. The direct bond in Formula XXXXIV and the Y groups are in the para position with respect to each other and each A, A', A", R, Y, n and p are as hereinbefore defined and q has a value from zero to about 6, preferably zero to about 3.

Suitable compounds which contain one or more rodlike mesogenic structure(s) and an average of one cyanate or cyanamide group per molecule represented by Formulas as XXXXII, XXXXIII, XXXX IV and XXXXV include, for example, the cyanates of 4-hydroxystilbene, 4-hydroxy-4'-methoxystilbene, 4-hydroxy-4'-chlorostilbene, 4-hydroxy-4'-nitrostilbene, 4- hydroxy-4'-cyanostilbene, 4-hydroxy-alpha-methylstilbene, 4-hydroxychalcone, 1-(4-hydroxyphenyl)-2-phenylacetylene, 1-(4-hydroxyphenyl)-2-phenylazomethine, 4-hydroxyphenylazobenzene, 4-hydroxyphenylazoxybenzene, 4-(4-hydroxyphenoxy)diphenyl, 4-hydroxydiphenyl, 4-hydroxy-alpha-cyanostilbene, 4-hydroxy-alpha-ethylstilbene, 4-hydroxybenzanilide, 4-hydroxy-4'-methoxybenzanilide, 4-hydroxy-3,3',5,5'-tetramethyl-alpha-methylstilbene, N-methyl-4-hydroxybenzamide, N-phenyl-4-hydroxybenzamide, 4-hydroxy-3,3',5,5'-tetrabromo-alpha-methylstilbene, 4-hydroxyphenylbenzoate, phenyl-4-hydroxybenzoate, the cyanamides of 4-aminostilbene, 4-amino-alpha-methylstilbene, 4-aminobenzanilide, and the like. The compounds which contain one or more rodlike mesogenic structure(s) and an average of one cyanate or cyanamide group per molecule are prepared using the corresponding monophenol (monoamine) containing one or more rodlike mesogenic structure(s) and the hereinbefore described chemistry used in the preparation of polycyanates (polycyanamides).

METHOD FOR FORMING THE MIXTURES OF THE PRESENT INVENTION

The mixtures of the present invention can be prepared by directly combining one or more of the desired component(s) with one or more polycyanates or polycyanamides containing one or more rodlike mesogenic structures or by addition of one or more of the desired components to the polycyanates or polycyanamides containing one or more rodlike mesogenic structures in increments or stages. When a single component is to be added to the polycyanates or polycyanamides containing one or more rodlike mesogenic structures, said component may be prepolymerized (B-staged) or fully homopolymerized, prior to the addition. Additionally, certain of said single components may be homopolymerized (interpolymerized) while dispersed in or mixed in with one or more polycyanates or polycyanamides containing one or more rodlike mesogenic structures. When two or more components are to be added to the polycyanates or polycyanamides containing one or more rodlike mesogenic structures, said components may be partially or totally copolymerized or reacted together, prior to the addition. Additionally, when two or more components are to be added to the polycyanates or polycyanamides containing one or more rodlike mesogenic structures, one component may be prepolymerized or fully homopolymerized in the presence of the other components, prior to the addition. It is understood that one or more catalysts or accelerators may be included where desired to facilitate the aforementioned copolymeriza-tion, interpolymerization, prepolymerization, homopolymerization or reaction of one or more specific components.

The mixtures of the thermosettable polycyanate or polycyanamide containing one or more rodlike mesogenic moieties (component A) and the components B-1 to B-12 can contain any amounts of components A and B. Suitably, the components are employed in amounts such that the mixture contains from about 1 to about 99, preferably from about 25 to about 95, more preferably from about 50 to about 90 percent by weight of component A based on the combined weight of components A and B; and from about 99 to about 1, preferably from about 75 to about 5, more preferably from about 50 to about 10 percent by weight based on the combined weight of components A and B.

POLYMERIZATION OF THE POLYMERIZABLE MIXTURES

The mixtures of the present invention may be polymerized by heating from about 50° C. to about 400° C., preferably by heating from 100° C. to 250° C., optionally in the presence of one or more suitable catalysts. In addition to the catalysts previously delineated for the polymerization of polycyanates or polycyanamides, whenever one or more polymaleimides, compounds containing one or more polymerizable ethylenically unsaturated group(s), compounds which simultaneously contain both a cyanate or cyanamide group and a polymerizable ethylenically unsaturated group, compounds which simultaneously contain both a 1,2-epoxide group and a polymerizable ethylenically unsaturated group or compounds which simultaneously contain both a maleimide group and a cyanate group it is often desireable to utilize one or more free radical forming catalysts for the purpose of polymerizing all or a part of said unsaturated groups. Said free radical forming catalysts include the organic peroxides and hydroperoxides as well as the azo and diazo compounds. Preferred free radical forming catalysts include benzoylperoxide, t-butylhydroperoxide, t-butylperoxybenzoate, azobisisobutyronitrile, dicumylperoxide, di-tert-butylperoxide and cumene hydroperoxide. The quantity of catalyst used, if any, depends on the structure of the particular catalyst, the structure of the components used in the polymerizable mixture, the cure structure desired, the cure time, the cure temperature, and the like. Generally, catalyst concentrations of from about 0.001 to about 2 percent by weight are preferred. B-staging or prepolymerization of the mixtures of the present invention can be accomplished by using lower temperatures and/or shorter curing times. Curing of the thus formed B-staged (prepolymerized) mixture can then be accomplished at a later time or immediately following B-staging (prepolymerization) by increasing the temperature and/or curing time.

The polymerized mixtures possess a variety of curing structures which depend, in part, upon the amounts and types of individual components used to prepare said mixture, the sequence of component addition and procedure used to prepare said mixture, the amounts and types of catalysts, if any, employed, the reaction times and temperatures, and the like.

Mixtures of (A) one or more polycyanates containing one or more rodlike mesogenic structures and no other moieties reactive with the cyanate group with (B-1) one or more polycyanates which do not contain rodlike mesogenic structures and/or prepolymers of either of the aforementioned types of polycyanates cure via cyclotrimerization of the cyanate moieties to provide the polytriazine thermoset. As a preferred embodiment of the present invention, addition of about 10 percent or more of a polycyanate containing one or more rodlike mesogenic structures to a polycyanate which does not contain rodlike mesogenic structures followed by polymerizing or curing provides a polytriazine with improved mechanical properties over those of the polytriazine obtained from curing or polymerizing of only the polycyanate which does not contain rodlike mesogenic structures.

Mixtures of (A) one or more polycyanates containing one or more rodlike mesogenic structures and no other moieties reactive with the cyanate group with (B-2) one or more epoxy resins using a 1 to 1 mole ratio of cyanate groups to epoxide groups polymerize to produce a complex structure. Increasing the mole ratio of cyanate to epoxide groups can be done to increase the relative amount of triazine groups in the cured product. A preferred embodiment of the present invention is the polymerization product of a polycyanate containing one or more rodlike mesogenic structures with an epoxy resin containing one or more rodlike mesogenic structures. The aforementioned polymerized product provides improved properties, notably increased glass transition temperature, relative to the polymerization product of a polycyanate containing one or more rodlike mesogenic structures with an epoxy resin which does not contain rodlike mesogenic structures.

Mixtures of (A) one or more polycyanates containing one or more rodlike mesogenic structures and no other moieties reactive with the cyanate group with (B-3) one or more polymaleimides can polymerize to produce a complex variety of structures including the triazine group resulting from cyclotrimerization of cyanate moieties

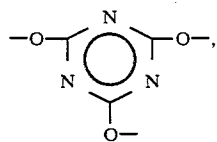

the maleimide group homopolymerization structure,

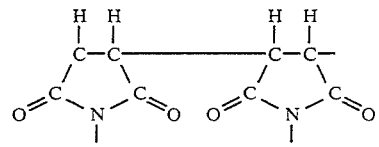

and cyanate group and maleimide group copolymerization structures such as, for example,

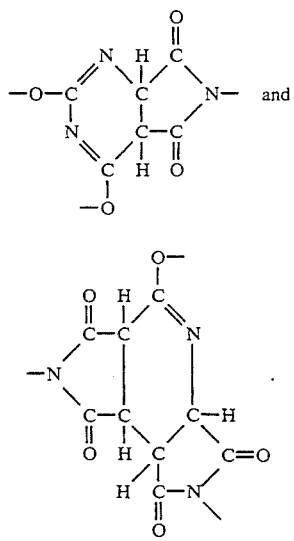

Changes in the mole ratio of cyanate groups and maleimide groups can be made to influence the composition of the cured product. Increasing the mole ratio of cyanate groups to maleimide groups to above 1 to 1 can be done to increase the relative amount of triazine groups in the polymerized product. A decrease in the mole ratio of cyanate groups to maleimide groups to below 1 to 1 favors an increase in the amount of maleimide group homopolymerization structure in the cured product. A preferred embodiment of the present invention is the polymerization product of a polycyanate containing one or more rodlike mesogenic structures with a polymaleimide containing one or more rodlike mesogenic structures. The aforementioned polymerized product provides improved mechanical properties relative to the polymerization product of a polycyanate containing one or more rodlike mesogenic structures with a polymaleimide which does not contain rodlike mesogenic structures. Methods for the copolymerization of polycyanates which do not contain rodlike mesogenic structures with polymaleimides are taught by U.S. Pat. Nos. 4,469,859; 4,404,330; 4,396,745; 4,383,903; 4,373,086; 4,371,689; 4,369,304; 4,287,014 and 4,110,364 which are incorporated herein by reference.

Mixtures of (A) one or more polycyanates containing one or more rodlike mesogenic structures and no other moieties reactive with the cyanate group with (B-4) one or more polyamines using a 1 to 1 mole ratio of cyanate groups to amine groups polymerize to produce poly(iminocarbamic acid esters). Increasing the mole ratio of cyanate to amine groups can be done to induce formation of triazine groups in the polymerized or cured product. Methods for the reaction of polyamino compounds with polycyanate compounds to produce poly(iminocarbamic acid esters) are taught by U.S. Pat.

No. 3,502,617 which is incorporated herein by reference.

Mixtures of (A) one or more polycyanates containing one or more rodlike mesogenic structures and no other moieties reactive with the cyanate group with (B-5) one or more polyphenols using a 1 to 1 mole ratio of cyanate groups to phenolic hydroxyl groups polymerize to produce poly(iminocarbonic acid esters). Increasing the mole ratio of cyanate to phenolic hydroxyl groups can be done to induce formation of triazine groups in the polymerized or cured product. Methods for the reaction of polyphenol compounds with polycyanate compounds to produce poly(iminocarbonic acid esters) are taught by U.S. Pat. No. 3,491,060 which is incorporated herein by reference.

Mixtures of (A) one or more polycyanates containing one or more rodlike mesogenic or structure(s) and no other moieties reactive with the cyanate group with (B-6) one or more polymerizable ethylenically unsaturated compounds can polymerize to produce a complex variety of structures including the triazine group resulting from cyclotrimerization of cyanate moieties, structure from the polymerization of the polymerizable ethylenically unsaturated compound(s) and cyanate group and polymerizable ethylenically unsaturated group copolymerization structures. A specific example of a structure arising from the copolymerization of cyanate groups with a vinyl aromatic group (styrene) is as follows:

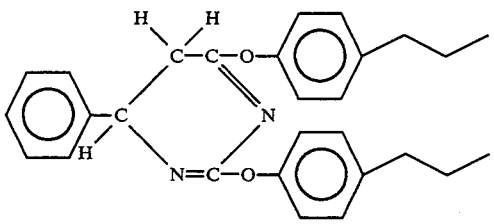

Changes in the mole ratio of cyanate groups and polymerizable ethylenically unsaturated groups can be made to influence the composition of the polymerized product. Increasing the mole ratio of cyanate groups to polymerizable ethylenically unsaturated groups to above 1 to 1 can be done to increase the relative amount of triazine groups in the polymerized product. A decrease in the mole ratio of cyanate groups to polymerizable ethylenically unsaturated groups to below 1 to 1 favors an increase in the amount of polymerizable ethylenically unsaturated group homopolymerization structure in the polymerized product. A preferred embodiment of the present invention is the polymerization product of a polycyanate containing one or more rodlike mesogenic structures with a polymerizable ethylenically unsaturated compound containing one or more rodlike mesogenic structures. The aforementioned polymerized product provides improved mechanical properties relative to the polymerization product of a polycyanate containing one or more rodlike mesogenic structures with a polymerizable ethylenically unsaturated compound which does not contain rodlike mesogenic structures. Methods for the copolymerization of a specific class of polycyanates which do not contain rodlike mesogenic structures with vinyl aromatic monomers are taught by U.S. Pat. No. 4,746,727 which is incorporated herein by reference.

Mixtures of (A) one or more polycyanates containing one or more rodlike mesogenic structures and no other moieties reactive with the cyanate group with (B-7) one or more compounds which simultaneously contain both a cyanate group and a polymerizable ethylenically unsaturated group or (B-8) one or more compounds which simultaneously contain both a 1,2-epoxide group and a polymerizable ethylenically unsaturated group or (B-9) one or more compounds which simultaneously contain both a maleimide group and a cyanate group can polymerize to produce a complex variety of structures, including those previously mentioned for the various respective functional groups. As a specific example, a preferred mixture of the present invention consists of the polymerization product of (B-7) one or more compounds which simultaneously contain both a cyanate group and a polymerizable ethylenically unsaturated group with (B-6) one or more compounds containing one or more ethylenically unsaturated groups. This copolymer is either prepared in situ by free radical initiated polymerization of the (B-6) and (B-7) components in a molten or solvent solution of (A) one or more polycyanates containing one or more rodlike mesogenic structures or it may be prepared separately then added to component (A). The resultant mixture is a polymer modified polycyanate which can be homopolymerized to provide the corresponding polymer modified polytriazine. In a further preferred embodiment of the present invention, if component (B-6) consists of one or more compounds containing ethylenically unsaturated groups and one or more rodlike mesogenic structures, liquid crystal polymer modified polycyanates and polytriazines thereof can be produced via the aforementioned technique. Preparation of polymer modified cyanates which do not contain rodlike mesogenic structures is taught by U.S. Pat. No. 4,559,399 which is incorporated herein by reference.

Mixtures of (A) one or more polycyanates containing one or more rodlike mesogenic structures with (B-10) one or more compounds which contain one or more rodlike mesogenic structures per molecule and only one cyanate (cyanamide) group per molecule can be cured via cyclotrimerization of the cyanate moieties to provide the polytriazine thermoset, providing that no other moieties reactive with cyanate groups are present in (A) or (B-10). Increasing the amount of the aforementioned cyanate compound containing an average of one cyanate group per molecule with respect to the amount of polycyanate can be used as a convenient method for lowering the crosslink density of the polytriazine product thereof.

ORIENTATION OF THE POLYMERIZED PRODUCT CONTAINING RODLIKE MESOGENIC STRUCTURES

During processing and/or curing of the polycyanates or polycyanamides containing one or more rodlike mesogenic structures or the mixtures containing said polycyanates or polycyanamides, electric or magnetic fields or shear stresses can be applied for the purpose of orienting the rodlike mesogenic moieties contained or developed therein. As specific examples of these methods, Finkelmann, et. al., *Macromol. Chem.*, 180, 803–806 (March, 1979), incorporated herein by reference, induced orientation in an electric field, of thermotropic methacrylate copolymers containing mesogenic side chain groups decoupled from the main chain via flexible spacers. Orientation in a magnetic field of mesogenic side chain groups decoupled from the main chain via flexible spacers has been demonstrated by Roth and Kruecke, *Macromol. Chem.*, 187, 2655–2662 (November, 1986) which is incorporated herein by reference. Magnetic field induced orientation of mesogenic main chain containing polymers has been demonstrated by Moore, et. al., *ACS Polymeric Material Sciences and Engineering*, 52, 84–86 (April-May, 1985) which is incorporated herein by reference. Magnetic and electric field induced orientation of low molecular weight mesogenic compounds is discussed by W. Krigbaum in *Polymer Liquid Crystals*, pages 275–309 (1982), published by Academic Press, Inc., and is incorporated herein by reference. The use of shear to induce orientation is also discussed therein. When the curing is to be performed in an electric or magnetic field, it is frequently of value to conduct simple preliminary experiments that allow for balancing of cure kinetics versus induction of orientation under the particular experimental conditions being employed (i.e. catalyst(s) level being used, temperature used, inherent dielectric (diamagnetic) susceptibility of the specific rodlike mesogenic structure(s) used, etc.). This is done recognizing the relatively greater ease of inducing orientation in low molecular weight materials versus polymeric materials containing rodlike mesogenic moieties.

In addition to orientation by electric or magnetic fields, the polycyanates or polycyanamides containing one or more rodlike mesogenic structures or mixtures containing said polycyanates or polycyanamides can be oriented by shear forces which are induced by flow through dies, orifices and mold gates. A general discussion of orientation of thermotropic liquid crystalline polymers by this method is given by S. K. Garg and S. Kenig in *High Modulus Polymers*, pages 71–103 (1988) published by Marcel Dekker, Inc. which is incorporated herein by reference. For the rodlike mesogen-containing polycyanates or mixtures containing said polycyanates, this shear orientation can conveniently be produced by or during processing methods such as injection molding, extrusion, pultrusion, filament winding, filming and prepreging.

OTHER COMPONENTS WHICH CAN BE EMPLOYED

The polycyanates or polycyanamides containing one or more rodlike mesogenic structures or mixtures containing said polycyanates or polycyanamides can be blended with other materials such as solvents or diluents, fillers including those comprising a liquid crystalline polymer, pigments, dyes, flow modifiers, thickeners, reinforcing agents, mold release agents, wetting agents, stabilizers, fire retardant agents, surfactants, low profile additives, shrinkage control agents, other resinous products, combinations thereof and the like.

These additives are added in functionally equivalent amounts, e.g., the pigments and/or dyes are added in quantities which will provide the composition with the desired color; however, they are suitably employed in amounts of from about zero to about 20, more suitably from about 0.5 to about 5, most suitably from about 0.5 to about 3 percent by weight based on the total weight of the composition.

Solvents or diluents which can be employed herein include, for example, hydrocarbons, ketones, aliphatic ethers, cyclic ethers, esters, chlorinated hydrocarbons, combinations thereof and the like. Particularly suitable solvents or diluents include, for example, toluene, xylenes, methylethyl ketone, methylisobutyl ketone, methylamyl ketone, chloroform, acetone, perchloroethylene, methylene chloride, tetrahydrofuran, 1,4-dioxane, ethyl acetate, butyl acetate, combinations thereof and the like.

The modifiers such as thickeners, flow modifiers, shrinkage control agents, low profile additives and the like can be suitably employed in amounts from about 0.05 to about 15, more suitably from about 0.1 to about 10, most suitably from about 0.1 to about 5 percent by weight based on the total weight of the composition.

Reinforcing materials which can be employed herein include natural and synthetic fibers in the form of woven fabric, mats, monofilament, multifilament, unidirectional fibers, rovings, random fibers or filaments, inorganic fillers or whiskers, hollow spheres, and the like. Suitable reinforceing materials include glass, ceramics, nylon, rayon, cotton, aramid, graphite, polyalkylene terephthlates, polyethylene, polypropylene, polyesters, carbon, boron, asbestos, combinations and hybrids thereof and the like.

Suitable fillers which can be employed herein include, for example, inorganic oxides, ceramic microspheres, plastic microspheres, glass microspheres, inorganic whiskers, calcium carbonate, graphite powder, sand, metal powders, combinations thereof and the like. The fillers can be employed in amounts from about 0.1 to about 95, more suitably from about 5 to about 80, most suitably from about 10 to about 50 percent by weight of the total composition.

USES FOR THE COMPOSITIONS

The compositions of the present invention can be employed in the preparation of laminates, prepregs, composites, coatings, castings, pultruded products, filament wound products, films, molding and potting formulations, injection molded products, and the like.

The following examples are illustrative of the invention but are not to be construed as to limiting the scope thereof in any manner.

EXAMPLE 1

A. Synthesis of 4,4'-Dihydroxy-alpha-methylstilbene

Phenol (376.44 grams, 4.0 moles), chloroacetone (205.62 grams, 2.0 moles as chloroacetone) and methylene chloride (300 grams) are added to a reactor and cooled to $-10°$ C. with stirring. The chloroacetone used is a technical grade containing 90% chloroacetone, 2.5% acetone, 6.5% 1,1-dichloroacetone and 1.0% 1,3-dichloroacetone. Concentrated sulfuric acid (196.16 grams, 2.0 mole) is added dropwise to the stirred solution over a one hour period and so as so maintain the reaction temperature at $-10°$ C. After two hours of post reaction at the $-10°$ C. temperature, the viscous orange oil solution is mixed with 500 milliliters of iced deionized water. The oil solution is separated then washed with a second 500 milliliter portion of iced deionized water. After separation, the recovered oil solution is added to a 2 liter beaker along with 250 milliliters of ethanol and stirred to provide a solution. Deionized water (250 milliliters) is added to the stirred solution and heating commenced. As the temperature of the mixture increased, the stirred mixture began to clear. Each time clearing is observed, sufficient deionized water is added to induce cloudiness, followed by continuation of the mixing and heating. Once the temperature reached 70° C., a massive precipitation of white crystalline plates occurred and is followed by immediate coalesence of the precipitated product to an oil. The oil layer is recovered by decantation of the water layer and 250 milliliters of ethanol is added. Deionized water is again added to the stirred solution as heating commenced, in an amount sufficient to induce cloudiness each time clearing is observed. Once the temperature reached 90° C., a massive precipitation of white crystalline plates again occurred. At this time, stirring is stopped and the crystalline slurry, as well as the decanted water layer are both chilled to 5° C. and held therein for 12 hours. The crystalline product is recovered by filtration then combined with 250 milliliters of deionized water then stirred with heating to 90° C. After cooling to 5° C., the crystalline product is recovered by filtration then dried in a vacuum oven at 100° C. and 5 mm Hg to a constant weight of 243.3 grams. Proton magnetic resonance spectroscopy and infrared spectrophotometric analysis confirmed the product structure.

B. Preparation of Dicyanate of 4,4'-Dihydroxy-alpha-methylstilbene 4,4'-Dihydroxy-alpha-methylstilbene (226.26 grams, 2.0 hydroxyl equivalents) prepared using the method of A above, cyanogen bromide (222.45 grams, 2.10 moles) and acetone (1200 milliliters) are added to a reactor and maintained under a nitrogen atmosphere with stirring. The stirred solution is cooled to −5° C., then triethylamine (203.39 grams, 2.01 moles) is added to the reactor over a 34 minute period and so as to maintain the reaction temperature at −5° to −3° C. After completion of the triethylamine addition, the reactor is maintained at −5° to −3° C. for an additional 45 minutes followed by addition of the reactor contents to 1 gallon of deionized water. After 5 minutes, the water and product mixture is multiply extracted with three 400 milliliter volumes of methylene chloride. The combined methylene chloride extract is washed with 250 milliliters of 0.05 percent by weight aqueous hydrochloric acid followed by washing with two 500 milliliter portions of deionized water, then drying over anhydrous sodium sulfate. The dry methylene chloride extract is filtered and solvent removed by rotary evaporation under a vacuum for 60 minutes at 100° C. The dicyanate of 4,4'-dihydroxy-alpha-methylstilbene (272.5 grams) is recovered in 98.64 percent yield as a mass of light tan colored crystalline needles. Infrared spectrophotometric analysis of a film sample of the product confirmed the product structure (disappearance of phenolic hydroxyl absorbance, appearance of cyanate absorbance (2236 and 2270 cm$^{-1}$, sharp)).

C. Characterization of the Dicyanate of 4,4'-Dihydroxy-alpha-methylstilbene for Liquid Crystallinity A portion (10.28 milligrams) of the dicyanate 4,4'-dihydroxy-alpha-methylstilbene from B above is analyzed by differential scanning calorimetry using a heating rate of 10° C. per minute and the indicated temperature ranges. The results are given in Table I.

TABLE I

| CYCLE DESIGNATION | OBSERVED TRANSITION TEMPERATURES (°C.) MIDPOINT/ RANGE | ENTHALPY (J/g) | COMMENTS |
| --- | --- | --- | --- |
| First heating (30 to 200° C.) | 81/52–90 | — | Single peak |
| First cooling (200 to 0° C.) | 42/56–28 | — | Single peak |
| Second heating (0 to 200° C.) | 70.8/50–74<br>79.4/74–88 | 26.52<br>17.57 | Two resolved peaks |
| Second cooling (200 to −50° C.) | 42/56–26 | 53.58 | Single peak |

TABLE I-continued

| CYCLE DESIGNATION | OBSERVED TRANSITION TEMPERATURES (°C.) MIDPOINT/ RANGE | ENTHALPY (J/g) | COMMENTS |
| --- | --- | --- | --- |
| Third heating (−50 to 150° C.) | unchanged from second heating | unchanged from second heating | unchanged from second heating |

Analysis of the dicyanate via cross polarized light microscopy is completed using a microscope equipped with a programmable hot stage using a heating rate of 10° C. per minute and 35× magnification. The results are given in Table II.

TABLE II

| CYCLE DESIGNATION | OBSERVED TRANSITION TEMPERATURES (°C.) | COMMENTS |
| --- | --- | --- |
| First Heating | 25 | Immobile crystals. |
|  | 67 | First fluidity noted. |
|  | 76 | Crystals moving in fluid, crystals are restructuring. |
|  | 82 | Isotropization complete. |
| First Cooling | 61 | First crystallization noted. |
|  | 58 | Immobile crystalline mass. |
| Second Heating | 25 | Immobile crystals. |
|  | 67 | First fluidity noted. |
|  | 76 | Crystals moving in fluid, crystals are restructuring. |
|  | 82 | Isotropization complete. |

D. Preparation of a Cured Polytriazine Casting from the Dicyanate of 4,4'-Dihydroxy-alpha-methylstilbene A 250.0 gram portion of the dicyanate of 4,4'-dihydroxy-alpha-methylstilbene from B above is heated to 100° C. to form a solution, cooled to 50° C., then 0.25 gram of cobalt naphthenate (6.0 percent active) is added and mixed in. This solution is reheated to 100° C., filtered, poured into a ⅛ inch mold, then placed in an oven and maintained at 125° C. for 2 hours, 177° C. for 4 hours, 200° C. for 4 hours then 250° C. for 2 hours. The transparent, light amber colored casting is demolded and used to prepare test pieces for tensile and flexural strength and modulus, tensile elongation and average Barcol hardness (934–1 scale). Mechanical properties of the tensile and flexural test pieces are determined using an Instron machine with standard test methods (ASTM D 638 and D 790). The results are reported in Table III.

COMPARATIVE EXPERIMENT A

A. Preparation of Bisphenol A Dicyanate 4,4'-Isopropylidene diphenol (456.60 grams, 4.0 hydroxyl equivalents), cyanogen bromide (444.91 grams, 4.20 moles) and acetone (1100 milliliters) are added to a reactor and maintained under a nitrogen atmosphere with stirring. The stirred solution is cooled to −5° C., then triethylamine (406.82 grams, 4.02 moles) is added over a 60 minute period and so as to maintain the reaction temperature at −5° to −3° C. After completion of the triethylamine addition, the reactor is maintained at −5° to −3° C. for an additional 25 minutes followed by addition of the reactor contents to 1.5 gallons of deionized water. After 5 minutes, the water and product mixture is multiply extracted with three 500 milliliter volumes of methylene chloride. The combined methylene chloride extract is washed with 500 milliliters of 0.05 percent by weight aqueous hydrochloric acid followed by washing with 500 milliliters of deionized water, then drying over anhydrous sodium sulfate. The dry methylene chloride extract is filtered and solvent removed by rotary evaporation under vacuum for 60 minutes at 100° C. The bisphenol A dicyanate (545.8 grams) is recovered in 98.1 percent yield as a tan colored crystalline solid. Infrared spectrophotometric analysis of a film sample of the product confirmed the product structure (disappearance of phenolic hydroxyl, absorbance, appearance of cyanate absorbance).

B. Preparation of a Cured Polytriazine Casting from Bisphenol A Dicyanate

A 200.0 gram portion of bisphenol A dicyanate prepared using the method of A above is heated to 100° C. to form a solution, cooled to 50° C., then 0.20 gram of cobalt naphthenate (6.0 percent active) is added and mixed in. This solution is reheated to 100° C. filtered, poured into a ⅛ inch mold, then placed in an oven and maintained at 125° C. for 2 hours, 177° C. for 4 hours, 200° C. for 4 hours, then 250° C. for 2 hours. The transparent, light amber colored casting is demolded and used to prepare test pieces which are tested using the method of Example 1-D. The results are reported in Table III.

TABLE III

| MECHANICAL PROPERTY | EXAMPLE 1-D | COMPARATIVE EXPERIMENT A-B |
|---|---|---|
| Barcol Hardness | 51 | 48 |
| Tensile Strength (psi) | 15,010 | 13,080 |
| Tensile Modulus (psi) | 549,301 | 510,336 |
| Elongation (%) | 3.87 | 3.26 |
| Flexural Strength (psi) | 24,442 | 19,176 |
| Flexural Modulus (psi) | 568,556 | 555,138 |

Examination of a portion of the polytriazine casting of Example 1-D using cross polarized light microscopy revealed birefringence. By way of contrast, no birefringence is observed in the casting of Comparative Experiment A-B.

EXAMPLE 2

Differential Scanning Calorimetry

A portion (8.0 milligrams) of the dicyanate of 4,4'-dihydroxy-alpha-methylstilbene catalyzed with cobalt naphthenate from Example 1-D above is analyzed by differential scanning calorimetry (DSC). A first heating from 25° to 325° C. is completed at a rate of 10° C. per minute under a stream of nitrogen flowing at 35 cubic centimeters per minute resulting in the exothermic curing of the dicyanate. Similarly, a second heating is completed, with the glass transition temperature for the cured polytriazine determined from the data of this heating. The results are reported in Table IV.

COMPARATIVE EXPERIMENT B

The method of Example 2 is repeated using a portion (7.7 milligrams) of bisphenol A dicyanate catalyzed with cobalt naphthenate from Comparative Experiment A-B. The results are reported in Table IV.

TABLE IV

| SAMPLE DESIGNATION | GLASS TRANSITION TEMPERATURE | | |
|---|---|---|---|
| | ONSET (°C.) | MIDPOINT (°C.) | END (°C.) |
| Example 1-D | 263.1 | 288.2 | 308.1 |
| Comparative Experiment A-B | 235.9 | 251.1 | 256.9 |

EXAMPLE 3

Sets of four flexural strength test pieces prepared from the castings of Example 1-D and Comparative Experiment A-B are weighed, then immersed in deionized water contained in individual jars and maintained at 92° C. The test pieces are weighed at the indicated intervals and the percent weight gain calculated as follows: 100 ((exposed weight−initial weight)/initial weight). An average of the percent weight gain is then calculated with the results reported in Table V.

TABLE V

| SAMPLE DESIGNATION | PERCENT WEIGHT GAIN (hours of exposure) | | | |
|---|---|---|---|---|
| | 24 | 48 | 72 | 94 |
| Example 1-D | 1.31 | 1.81 | 2.12 | 2.30 |
| Comparative Experiment A-B | 1.93 | 2.37 | 2.57 | 2.69 |

EXAMPLE 4

A. Synthesis of bis(4'-Hydroxyphenyl)-1,4-benzenediimine p-Aminophenol (327.4 grams, 3.00 moles) and methanol (1300 milliliters) are added to a 2 liter round bottom flask with stirring. Terephthaldehyde (201.2 grams, 1.50 moles) is added to the reactor followed by heating to 50° C. After 3 hours at 50° C., the reaction mixture is vacuum filtered and the solids thus obtained are washed with methanol (500 milliliters). The washed solids are added back to the reactor along with additional methanol (1300 milliliters) and then heated with stirring to reflux. After refluxing for one hour, the mixture is again vacuum filtered with the recovered solids again added back to the reactor along with fresh methanol (950 milliliters). After refluxing for one hour, the mixture is vacuum filtered and the solids thus recovered are dried at 80° C. for four hours in a vacuum oven to a constant weight. The product is recovered (423.4 grams) as a light yellow colored powder in 89.2 percent yield. Differential scanning calorimetry of a portion of the product revealed a sharp melting point endotherm at 270° C. Infrared spectrophotometric analysis of a film of a nujol mull of a portion of the product confirmed the structure phenolic hydroxyl absorbance (3370 cm$^{-1}$, broad), —CH=N— stretching absorbance (1618 cm$^{-1}$, sharp)).

B. Preparation of Dicyanate of bis(4'-Hydroxyphenyl)-1,4-benzenediimine bis(4'-Hydroxyphenyl)-1,4-benzenediimine (137.85 grams, 0.8716 hydroxyl equivalent) from A above, cyanogen bromide (96.94 grams, 0.915 mole) and acetone (1000 milliliters) are added to a reactor and maintained under a nitrogen atmosphere with stirring. The stirred solution is cooled to −5° C., then triethylamine (89.08 grams, 0.8803 moles) is added to the reactor over a 33 minute period and so as to maintain the reaction temperature at −5° to −3° C. After completion of the triethylamine addition, the reactor is maintained at −5° C. to −3° C. for an additional 45 minutes followed by addition of the reactor contents to 1 gallon of deionized water. After 5 minutes, the water and product mixture is filtered through a fritted glass funnel and the resultant cake of yellow powder is washed by slurrying into 250 milliliters of deionized water. A second filtration recovered the yellow powder which is washed by slurring into 250 milliliters of methylene chloride. A third filtration recovered the yellow powder which is washed for a final time by slurring into 500 milliliters of deionized water followed by filtration to recover the yellow powder product. The dicyanate of bis(4'-hydroxyphenyl)-1,4-benzenediimine (155.1 grams) is recovered in 97.16 percent yield as a light yellow colored powder after drying at 100° C. in a vacuum oven to constant weight. Infrared spectrophotometric analysis of a nujol mull of a portion of the product confirmed the product structure (disappearance of phenolic hydroxyl absorbance (3370 cm$^{-1}$, broad), appearance of cyanate absorbance (2234 and 2272 cm$^{-1}$, sharp) retention of the —CH=N— stretching absorbance (1620 cm$^{-1}$, sharp)).

C. Evaluation of the Curing Behavior of the Dicyanate of bis(4'-Hydroxyphenyl)-1,4-benzenediimine Using Differential Scanning Calorimetry and Infrared Spectrophotometric Analysis A portion (8.75 milligrams) of the dicyanate of bis(4'-hydroxyphenyl)-1,4-benzenediimine (uncatalyzed) from B above is analyzed by differential scanning calorimetry (DSC). Heating from 25° to 330° C. is completed at a rate of 10° C. per minute under a stream of nitrogen flowing at 35 cubic centimeters per minute resulting in the exothermic curing of the dicyanate. The results are reported in Table VI.

TABLE VI

| DESCRIPTION OF TRANSITION | ONSET (°C.) | MIDPOINT (°C.) | END (°C.) |
|---|---|---|---|
| Exotherm (minor) | 126 | 191 | 206[1] |
| Exotherm (major) | 206 | 213 | 238 |

[1]End of first exotherm merges into the second exotherm.

The cured product is recovered from the differential scanning calorimetry as a yellow powder and is used to prepare a nujol mull. Infrared spectrophotometric analysis of a film of the nujol mull on a sodium chloride plate revealed that complete disappearance of the cyanate absorbance had occurred with retention of —CH=N— stretching absorbance and appearance of a new absorbance at 1560 cm$^{-1}$ attributed to the presence of the triazine ring.

D. Evaluation of the Curing Behavior of the Dicyanate of bis(4'-hydroxyphenyl)-1,4-benzenediimine Using Optical Microscopy A portion of the dicyanate of bis(4'-hydroxyphenyl)-1,4-benzenediimine from B above is placed between two glass slides and heated on a hot stage. During this heating, observations relating to changes in the morphology of the dicyanate are made at 35× magnification using a cross polarized light source. At a heating rate of 20° C. per minute, no melt for the dicyanate is observed up to 280° C. However, when a second sample of the dicyanate between glass slides is introduced on to the hot stage preheated to 250° C., melt flow is observed. After melt occurred, a birefringent morphology is produced. Curing followed the melt within 30 seconds with retention of birefringence in the solid. Another sample of the dicyanate between glass slides is introduced on to the hot stage preheated to 250° C. After melt had occurred, shear is applied to the sample by moving the top glass slide back and forth. With the application of shear, a shimmering fluorescence is produced. After the sample had solidified, birefringent striations are also observed which are oriented in the same direction that the shear is applied.

E. Preparation of Cured Dicyanate of bis(4'-Hydroxyphenyl)-1,4-benzenediimine for Thermal Mechanical Analysis A portion (0.71 gram) of the dicyanate of bis(4'-hydroxyphenyl)-1,4-benzenediimine from B above is placed in an aluminum pan which had been coated with a mold release. The aluminum pan is then put in a forced air convection type oven preheated to 250° C. Within the first minute in the oven, melt flow followed by thermosetting is observed. After 4 hours at 250° C., the oven is allowed to slowly cool to room temperature (25° C.) then the cured layer is removed from the pan. Optical microscopy of the cured product at 70× magnification using a cross polarized light source revealed extensive birefringence. Glass transition temperature and the mean linear thermal coefficient of expansion over the range from 35° C. to Tg are evaluated using a portion of the cured product. In this analysis, a constant probe force of 0.1 Newtons and a heating rate of 10° C. per minute are used over a range of 25° to 325° C. These results are reported in Table IX for both the initial and a second heating of the same sample.

EXAMPLE 5

Preparation of a Blend of the Dicyanate of bis(4'-Hydroxyphenyl)-1,4-benzenediimine and the Polycyanate of a Dicyclopentadiene Phenolic Novolac: Evaluation of Curing Behavior Using Differential Scanning Calorimetry and Thermal Mechanical Analysis of the Cured Blend A portion (0.88 gram) of the dicyanate of bis(4'-hydroxyphenyl)-1,4-benzenediimine from Example 4-B and 1.77 grams of a 2.2 cyanate functional polycyanate of a dicyclopentadiene phenolic novolac (uncatalyzed) from the same lot as Comparative Experiment C are mixed in an aluminum pan in a 100° C. oven. A paste is formed, a portion (15.0 milligrams) is analyzed by differential scanning calorimetry (DSC). Heating from 25° to 330° C. is completed at a rate of 10° C. per minute under a stream of nitrogen flowing at 35 cubic centimeters per minute resulting in exothermic curing. The results are reported in Table VII.

TABLE VII

| DESCRIPTION OF TRANSITION | ONSET (°C.) | MIDPOINT (°C.) | END (°C.) |
|---|---|---|---|
| Exotherm (enthalpy = −375 J/g) | 165 | 217 | 280 |

The differential scanning calorimetry results may be compared with those shown for the neat dicyanate of bis(4'-hydroxyphenyl)-1,4-benzenediimine in Example 4-C (Table VI) and the neat polycyanate of the dicyclopentadiene phenolic novolac in Comparative Experiment C (Table VIII). When compared to the neat polycyanate of the dicyclopentadiene phenolic novolac in Comparative Experiment C, the addition of the dicyanate of bis(4'-hydroxyphenyl)-1,4-benzenediimine to form the present blend has reduced the onset temperature to the curing exotherm by 35° C. and the curing exotherm peak temperature by 79° C.

Immediately after removal of the sample for differential scanning calorimetry, the aluminum pan is placed in a forced air, convection type oven preheated to 250° C. Within two minutes in the oven, melt flow followed by thermosetting is observed. After 4 hours at 250° C., the oven is allowed to slowly cool to room temperature (25° C.) then the cured layer removed from the pan. Glass transition temperature and the mean linear thermal coefficient of expansion over the range from 35° C. to Tg are evaluated using a portion of the cured product. In this analysis, a constant probe force of 0.1 Newtons and a heating rate of 10° C. per minute are used over a range of 25° to 325° C. These results are reported in Table IX for both the initial and a second heating of the same sample.

COMPARATIVE EXPERIMENT C

Evaluation of the Curing Behavior of the Polycyanate of a Dicycpentadiene Phenolic Novolac and Thermal Mechanical Analysis of the Cured Polytriazine 15.0 milligrams of a commercial grade 2.2 cyanate functional polycyanate of a dicyclopentadiene phenolic novolac (uncatalyzed) is analyzed by differential scanning calorimetry (DSC). Heating from 25° to 330° C. is completed at a rate of 10° C. per minute under a stream of nitrogen flowing at 35 cubic centimeters per minute resulting in exothermic curing. The results are reported in Table VIII.

TABLE VIII

| DESCRIPTION OF TRANSITION | ONSET (°C.) | MIDPOINT (°C.) | END (°C.) |
|---|---|---|---|
| Exotherm (enthalpy = −354 J/g) | 200 | 296 | 315 |

1.93 grams of the polycyanate of a dicyclopentadiene phenolic novolac is placed in an aluminum pan. The aluminum pan is then put in a forced air convection type oven preheated to 250° C. After twenty minutes in the oven thermosetting is observed. After 4 hours at 250° C., the oven is allowed to slowly cool to room temperature (25° C.) then the cured layer removed from the pan. Optical microscopy of the cured product at 70× magnification using a cross polarized light source revealed a minor amount of birefringence. Glass transition temperature and the mean linear thermal coefficient of expansion over the range from 35° C. to Tg are evaluated using a portion of the cured product. In this analysis, a constant probe force of 0.1 Newtons and a heating rate of 10° C. per minute are used over a range of 25° to 325° C. These results are reported in Table IX for both the initial and a second heating of the same sample.

EXAMPLE 6

Preparation of a Cured Polytriazine Casting from a Blend of Bisphenol A Dicyanate and the Dicyanate of bis(4'-Hydroxyphenyl)-1,4-benzenediimine A 175.0 gram portion of bisphenol A dicyanate prepared using the method of Comparative Experiment A-A and a 25.0 gram portion of the dicyanate of bis(4'-hydroxyphenyl)-1,4-benzenediimine from Example 4-B are heated to 145° C. to form a solution, then further heated to 150° C. and held therein for 10 minutes. The resulting B-staged resin solution is filtered while hot through a heated fritted glass funnel. This solution is then poured into a ⅛ inch mold, then placed in an oven and maintained at 125° C. for 2 hours, 177° C. for 4 hours, 200° C. for 4 hours, then 250° C. for 2 hours. The transparent, light amber colored casting is demolded and used to prepare test pieces which are tested using the method of Example 1-D. The results are reported in Table X and may be compared with those obtained for Comparative Experiment A-B reported in Table III.

TABLE X

| MECHANICAL PROPERTY | EXAMPLE 6 |
|---|---|
| Barcol Hardness | 51 |
| Tensile Strength (psi) | 12,753 |
| Tensile Modulus (psi) | 564,869 |
| Elongation (%) | 3.09 |
| Flexural Strength (psi) | 23,475 |
| Flexural Modulus (psi) | 588,060 |

EXAMPLE 7

Differential Scanning Calorimetry

The method of Example 2 is repeated using a portion (8.6 milligrams) of the bisphenol A dicyanate and dicyanate of bis(4'-hydroxyphenyl)-1,4-benzenediimine blend from Example 6. The results from the second heating are reported in Table XI and may be compared with those reported for Comparative Experiment A-B reported in Table IV.

TABLE XI

| SAMPLE DESIGNATION | GLASS TRANSITION TEMPERATURE | | |
|---|---|---|---|
| | ONSET (°C.) | MIDPOINT (°C.) | END (°C.) |
| Example 7 | 255.5 | 263.4 | 277.6 |

TABLE IX

| | DESIGNATION OF SAMPLE | | |
|---|---|---|---|
| | EXAMPLE 4-E | EXAMPLE 5 | COMPARATIVE EXPERIMENT C |
| Dicyanate of bis(4'-hydroxyphenyl)-1,4-benzenediimine/polycyanate of dicyclopentadiene phenolic novolac (wt. %) | 100/0 | 33.2/66.8 | 0/100 |
| Thermal Mechanical Analysis: | | | |
| Tg (first heat) (°C.) | 285 | 258 | 240 |
| Tg (second heat) (°C.) | >325 | 311 | 237 |
| Mean linear coefficient of thermal expansion (first heat) (ppm/°C.) | 53 | 52 | 58 |
| Mean linear coefficient of thermal expansion (second heat) (ppm/°C.) | 52 | 54 | 55 |

EXAMPLE 8

Differential Scanning Calorimetry of Blends of the Dicyanate of 4,4'-Dihydroxy-alpha-methylstilbene and Various Epoxy Resins Blend A A portion (0.5525 gram, 0.004 cyanate equivalent) of the dicyanate of 4,4'-dihydroxy-alpha-methylstilbene from Example 1-D above, a commercial grade diglycidyl ether of bisphenol A (179.95 epoxide equivalent weight) (0.7198 gram, 0.004 epoxide equivalent) and cobalt naphthenate (0.0013 gram, 0.1% wt.) are blended then gently heated to form a homogeneous solution.

Blend B

A portion (0.4144 gram, 0.003 cyanate equivalent ) of the dicyanate of 4,4'-dihydroxy-alpha-methylstilbene from Example 1-D above, the diglycidyl ether of 4,4'-dihydroxy-alpha-methylstilbene (177.61 epoxide equivalent weight) (0.5328 gram, 0.003 epoxide equivalent) and cobalt naphthenate (0.001 gram, 0.1% wt.) are blended then gently heated to form a homogeneous solution.

Portions (9.4 and 8.8 milligrams, respectively) of the aforementioned blends are analyzed by differential scanning calorimetry using the method of Example 2. The results from the second heating are reported in Table XII.

TABLE XII

| SAMPLE DESIGNATION | GLASS TRANSITION TEMPERATURE | | |
|---|---|---|---|
| | ONSET (°C.) | MIDPOINT (°C.) | END (°C.) |
| Example 8, Blend A | 172.0 | 188.3 | 204.3 |
| Example 8, Blend B | 208.5 | 215.7 | 221.1 |

EXAMPLE 9

Differential Scanning Calorimetry of A Blend of the Dicyanate of 4,4'Dihydroxy-alpha-methylstilbene and p-Vinyltoluene A portion (0.70 gram, 70.0 % wt.) of the dicyanate of 4,4'-dihydroxy-alpha-methylstilbene from Example 1-D above, p-vinyltoluene (0.30 gram, 30 % wt.) and cobalt naphthenate (0.001 gram, 0.1% wt.) are blended then gently heated to form a homogeneous solution. A portion (9.5 milligrams) of the aforementioned blend is analyzed by differential scanning calorimetry using the method of Example 2. The results from the second heating are reported in Table XIII.

TABLE XIII

| SAMPLE DESIGNATION | GLASS TRANSITION TEMPERATURE | | |
|---|---|---|---|
| | ONSET (°C.) | MIDPOINT (°C.) | END (°C.) |
| Example 9 | 264.4 | 289.2 | 309.2 |

EXAMPLE 10

A. Synthesis of 4,4'-Dihydroxybenzanilide 4,4'-dihydroxybenzophenone (100.0 grams, 0.467 mole) is added to ethanol (300 milliliters) in a 1 liter Erlenmeyer flask and stirred. After dissolution of the 4,4'-dihydroxybenzophenone, a solution of hydroxylamine hydrochloride (48.6 grams, 0.699 mole) and sodium acetate (57.4 grams, 0.700 mole) in deionized water (70 milliliters) is added followed by an additional 100 milliliters of ethanol. This mixture is stirred and heated on a hot plate to a gentle reflux (75° C.). After heating for 4 hours, the solution is allowed to cool to room temperature (25° C.) with stirring and then filtered. The filter cake is washed with ethanol (100 milliliters); then the total filtrant obtained (600.4 grams) is concentrated to a weight of 219.2 grams by evaporation of the ethanol and water. The concentrated solution is placed into a 1 liter Erlenmeyer flask then stirred as 600 milliliters of deionized water is added. The addition of the deionized water induced formation of a white precipitate. After thirty minutes of stirring, the mixture is filtered. The solid 4,4'-dihydroxybenzophenone oxime thus obtained weighed 98.22 grams after drying. 4,4'-Dihydroxybenzophenone oxime (66.0 grams. 0.288 mole) and glacial acetic acid (330 milliliters) are added to a 500 milliliter round bottom flask equipped with a stirrer, water cooled condensor, nitrogen purge and heating mantle. A catalytic amount of p-toluenesulfonic acid (1.85 grams, 0.027 mole) is added and the reaction mixture then heated to 83° C. After heating for approximately two hours, a precipitate formed and the mixture is stirred for an additional two hours at 87° C. After this time, 25 milliliters of deionized water is added to the reactor and after thirty minutes, the contents of the reactor is transferred to a 1 liter Erlenmeyer flask and maintained therein with stirring. Immediately following the transfer, 400 milliliters of deionized water is added to the flask. The mixture is stirred for forty five minutes and then filtered. The filter cake thus obtained is washed with 800 milliliters of deionized water and then dried. The resultant light beige colored solid weighed 54.82 grams. Fourier transform infrared spectrophotometric analysis of a portion of the product confirmed the product structure as that of 4,4'-dihydroxybenzanilide. Differential scanning calorimetry demonstrated a sharp melting point endotherm at 273° C. for the 4,4'-dihydroxybenzanilide product.

B. Preparation of Dicyanate of 4,4'-Dihydroxybenzanilide 4,4'-Dihydroxybenzanilide (32.0 grams, 0.2792 hydroxyl equivalent) from A above, cyanogen bromide (32.53 grams, 0.3071 mole) and acetone (500 milliliters) are added to a reactor and maintained under a nitrogen atmosphere with stirring. The stirred solution is cooled to −5° C., then triethylamine (28.54 grams, 0.2820 mole) is added to the reactor over a 20 minute period and so as to maintain the reaction temperature at −5° to −3° C. After completion of the triethylamine addition, the reactor is maintained at −5° to −3° C. for an additional 45 minutes followed by addition of the reactor contents to 1 gallon of deionized water. After 2 minutes of agitation the water and product mixture is filtered through a fritted glass funnel to remove a cake of white crystalline product. The filter cake is washed with 500 milliliters of deionized water, recovered by filtration, and again washed with 500 milliliters of deionized water. The cake recovered from a final filtration is dried at 80° C. in a vacuum oven to a constant weight of 37.55 grams (96-33% isolated yield). Infrared spectrophotometric analysis of a film sample of the product confirmed the product structure (presence of amide N-H stretching (3403 cm$^{-1}$, sharp), presence of amide I carbonyl stretching in solid state (1681 cm$^{-1}$), disappearance of phenolic hydroxyl absorbance, appearance of cyanate absorbance (2273 and 2232 cm$^{-1}$, sharp).

C. Evaluation of the Curing Behavior of the Dicyanate of 4,4'-Dihydroxybenzanilide Using Differential Scanning Calorimetry and Infrared Spectrophotometric Analysis A portion (11.40 milligrams) of the dicyanate of 4,4'-dihydroxybenzanilide (uncatalyzed) from B above is analyzed by differential scanning calorimetry (DSC). Heating from 25° to 250° C. is completed at a rate of 10° C. per minute under a steam of nitrogen flowing at 35 cubic centimeters per minute resulting in exothermic curing of the dicyanate. The results are reported in Table XIV.

TABLE XIV

| DESCRIPTION OF TRANSITION | ONSET (°C.) | MIDPOINT (°C.) | END (°C.) |
|---|---|---|---|
| Endotherm (minor) | 179 | 187 | 191 |
| Exotherm (enthalpy = −359 J/g) | 191 | 199 | 209 |

The cured product is recovered from the differential scanning calorimetry as a light amber colored solid and is used to prepare a nujol mull. Infrared spectrophotometric analysis of a film sample of the nujol mull on a sodium chloride plate revealed that complete disappearance of the cyanate absorbance, the amide carbonyl stretch and the amide N-H stretch had occurred with appearance of new absorbances at 1743, 1654 and 1560 cm$^{-1}$ (1560 cm$^{-1}$ is attributed to the presence of the triazine ring).

D. Evaluation of the Curing Behavior of the Dicyanate of 4,4'-Dihydroxybenzanilide Using Optical Microscopy A portion of the dicyanate of 4,4'-dihydroxybenzanilide from B above is placed between two glass slides and heated on a hot stage. During this heating, observations relating to changes in the morphology of the dicyanate are made at 35× magnification using a cross polarized light source. At a heating rate of 10° C. per minute melt flow is observed at 184° C. and resulted in a birefringent texture. Curing followed the melt once the temperature reached 187° C. On cooling to room temperature (25° C.) extensive birefringence is observed in the thermoset product. Another sample of the dicyanate between glass slides is introduced on to the hot stage preheated to 190° C. Within one minute melt had occurred then shear is applied to the sample by moving the top glass slide back and forth. After less than an additional 30 seconds, the sample had solidified and the hot stage is cooled to room temperature at a rate of 10° C. per minute. At room temperature, birefringent striations are also observed which are oriented in the same direction that the shear is applied. Upon reheating of the thermoset at a rate of 10° C., the birefringent striations remained up to 250° C. at which temperature heating is discontinued.

E. Preparation of Cured Dicyanate of 4,4'-Dihydroxybenzanilide for Thermal Mechanical Analysis A portion (0.50 gram) of the dicyanate of 4,4'-dihydroxybenzanilide from B above is placed in an aluminum pan. The aluminum pan is then put in a forced air convection type oven preheated to 190° C. Within the first five minutes in the oven, melt flow followed by thermosetting is observed. After 5 minutes at 190° C., the oven temperature is raised to 250° C. and maintained therein for four hours before the oven is allowed to slowly cool to room temperature (25° C.); then the cured layer removed from the pan. Optical microscopy of the cured product at 70× magnification using a cross polarized light source revealed extensive birefringence. Glass transition temperature and the mean linear thermal coefficient of expansion over the range from 35° C. to Tg are evaluated using a portion of the cured product. In this analysis, a constant probe force of 0.1 Newtons and a heating rate of 10° C. per minute are used over a range of 25° to 325° C. These results are reported in Table XVI.

EXAMPLE 11

Preparation of a Blend of the Dicyanate of 4,4'-Dihydroxybenzanilide and the Polycyanate of a Dicyclopentadiene Phenolic Novolac: Evaluation of Curing Behavior Using Differential Scanning Calorimetry and Thermal Mechanical Analysis of the Cured Blend A portion (0.88 gram) of the dicyanate of 4,4'-dihydroxybenzanilide from Example 10-B and 1.72 grams of a polycyanate of a dicyclopentadiene phenolic novolac (uncatalyzed) from the same lot as Comparative Experiment C are mixed in an aluminum pan contained in a 100° C. oven. From the paste formed, a portion (15.0 milligrams) is analyzed by differential scanning calorimetry (DSC). Heating from 25° to 330° C. is completed at a rate of 10° C. per minute under a stream of nitrogen flowing at 35 cubic centimeters per minute resulting in exothermic curing. The results are reported in Table XV.

TABLE XV

| DESCRIPTION OF TRANSITION | ONSET (°C.) | MIDPOINT (°C.) | END (°C.) |
|---|---|---|---|
| Exotherm (enthalpy = −459 J/g) | 165 | 212 | 240 |

The differential scanning calorimetry results may be compared with those shown for the neat dicyanate of 4,4'-dihydroxybenzanilide in Example 10-C (Table XIV) and the neat polycyanate of the dicyclopentadiene phenolic novolac in Comparative Experiment C (Table VIII). When compared to the neat polycyanate of the dicyclopentadiene phenolic novolac in Comparative Experiment C, the addition of the dicyanate of 4,4'-dihydroxybenzanilide to form the present blend has reduced the onset temperature of the curing exotherm by 35° C. and the curing exotherm peak temperature by 84° C.

Immediately after removal of the sample for differential scanning calorimetry, the aluminum pan is placed in a forced air, convection type oven preheated to 190° C. Within fifteen minutes in the oven, melt flow followed by thermosetting is observed. After 3 hours at 190° C., the oven temperature is raised to 232° C. and maintained therein for two hours before the oven is allowed to slowly cool to room temperature (25° C.) then the cured layer removed from the pan. Glass transition temperature and the mean linear thermal coefficient of expansion over the range from 35° C. to Tg are evaluated using a portion of the cured product. In this analysis, a constant probe force of 0.1 Newtons and a heating rate of 10° C. per minute are used over a range of 25° to 325° C. These results are reported in Table XVI.

COMPARATIVE EXPERIMENT D

Thermal Mechanical Analysis of the Cured Polytriazine of a Polycyanate of a Dicyclopentadiene Phenolic Novolac Use of a Different Cure Schedule 2.57 grams of the polycyanate of a dicyclopentadiene phenolic novolac from the same lot as Comparative Experiment C is placed in an aluminum pan. The aluminum pan is then put in a forced air convection type oven preheated to 190° C. After three hours at 190° C., the oven temperature is raised to 232° C. and maintained therein for two hours before the oven is allowed to slowly cool to room temperature (25° C.); then the cured layer is removed from the pan. Optical microscopy of the cured product at 70× magnification using a cross polarized light source revealed a minor amount of birefringence. Glass transition temperature and the mean linear thermal coefficient of expansion over the range from 35° C. to Tg are evaluated using a portion of the cured product. In this analysis, a constant probe force of 0.1 Newtons and a heating rate of 10° C. per minute are used over a range of 25° to 325° C. These results are reported in Table XVI.

The product left in the funnel from the first filtration (of the pulverized solid product boiled in 200 milliliters of methanol) is stirred in methanol (500 milliliters) and brought to a boil. After boiling for 15 minutes, the slurry is filtered while still hot. The white product recovered on the filter is dried under vacuum for 12 hours at 90° C. to a constant weight of 31.8 grams. Fourier transform infrared spectrophotometric analysis of a potassium chloride pellet of the product confirms the product structure for bis(4'-hydroxybenzoyl)-1,4-dihydroxybenzene. Differential scanning calorimetry of a portion of the product (23.5 milligrams) heated at 10° C. per minute under nitrogen flowing at 35 cubic centimeters per minute reveals a sharp melting point endotherm

TABLE XVI

| | DESIGNATION OF SAMPLE | | |
|---|---|---|---|
| | EXAMPLE 10-E | EXAMPLE 11 | COMPARATIVE EXPERIMENT D |
| Dicyanate of 4,4'-Dihydroxybenzanilide/Polycyanate of Dicyclopentadiene Phenolic Novolac (wt. %) | 100/0 | 33.1/66.9 | 0/100 |
| Thermal Mechanical Analysis: | | | |
| Tg (°C.) | 242 | 240 | 239 |
| Mean linear coefficient of thermal expansion (ppm/°C.) | 35 | 36 | 46 |

EXAMPLE 12

A. Synthesis of 4'-Hydroxyphenyl-4-hydroybenzoate and bis(4'-Hydroxybenzoyl)-1,4-dihydroxybenzene Hydroquinone (286.0 grams, 2.6 mole), p-hydroxybenzoic acid (179.4 grams, 1.3 mole), diethylbenzene (52 grams) and p-toluenesulfonic acid (0.64 gram) are added to a one liter glass resin kettle reactor and heated to 200° C. with stirring under a nitrogen atmosphere flowing at a rate of one liter per minute. The reactant slurry becomes an amber colored solution once the reaction temperature reaches 165° C. Water and diethylbenzene azeotropically distil from the reactor and are collected in a Dean Stark trap interspersed between the reactor and a chilled water condenser. After 45 minutes at the 200° C. reaction temperature, distillation ceases, and the reaction product is poured into an aluminum foil tray. The resultant solid product is ground to a fine powder then stirred in methanol (1200 milliliters) and brought to a boil. After boiling for 15 minutes, the slurry is filtered while still hot. Deionized water (6 liters) is added to the recovered methanol solution and the resultant white precipitate is recovered by filtration. The precipitate is redissolved in stirred, boiling methanol (1200 milliliters), then reprecipitated via the addition of deionized water (6 liters). The resultant white precipitate recovered by filtration is dissolved a third time in stirred, boiling methanol (1000 milliliters), then the solution cooled to room temperature (25° C.) and filtered. Reprecipitation is completed by addition of the filtered solution to deionized water (5 liters). The white precipitate is recovered by filtration then dried under vacuum for 12 hours at 90° C. to a constant weight of 125.1 grams. Fourier transform infrared spectrophotometric analysis of a potassium chloride pellet of the product and high pressure liquid chromatographic analysis confirm the product structure for 4'-hydroxyphenyl-4-hydroxybenzoate. Differential scanning calorimetry of a portion of the product (17 milligrams) heated at 10° C. per minute under nitrogen flowing at 35 cubic centimeters per minute reveals a sharp melting point endotherm with a minimum at 246.8° C.

with a minimum at 332.3° C.

B. Preparation of Dicyanate of 4'-Hydroxyphenyl-4-hydroxybenzoate

4'-Hydroxyphenyl-4-hydroxybenzoate (11.51 grams, 0.10 hydroxyl equivalents) from A above, cyanogen bromide (11.12 grams, 0.105 moles) and acetone (350 milliliters) are added to a reactor and maintained under a nitrogen atmosphere with stirring. The stirred solution is cooled to −2° C., then triethylamine (10.22 grams, 0.101 mole) is added to the reactor over a ten minute period and so as to maintain the reaction temperature at −3° to 0° C. After completion of the triethylamine addition, the reactor is maintained at −2° to 0° C. for an additional 45 minutes followed by addition of the reactor contents to deionized water (3 liters). After 2 minutes, the water and product mixture is filtered through a fritted glass funnel and the resultant cake of white powder is washed by slurrying into 300 milliliters of deionized water. A second filtration recovered the white powder which is again washed by slurrying into 300 milliliters of deionized water. A third filtration recovered the white powder which is then dried in a vacuum oven at 80° C. and 1 mm Hg to a constant weight of 13.8 grams. Fourier transform infrared spectrophotometric analysis of a potassium bromide pellet of product confirmed the product structure (disappearance of phenolic hydroxyl absorbance, appearance of cyanate absorbance (2234 and 2273 cm$^{-1}$, (sharp)).

C. Evaluation of the Curing Behavior of the Dicyanate of 4'-Hydroxyphenyl-4-hydroxybenzoate using Differential Scanning Calorimetry A portion (8.80 milligrams) of the dicyanate of 4'-hydroxyphenyl-4-hydroxybenzoate from B above is analyzed by differential scanning calorimetry. A first heating from 30° to 300° C. is completed at a rate of 10° C. per minute under a stream of nitrogen flowing at 35 cubic centimeters per minute resulting in exothermic curing of the dicyanate. The results are given in Table XVII. Similarly, a second heating is completed, with no glass transition temperature or any other thermal event being detected between the 30° to 300° C. range of the analysis.

TABLE XVII

| DESCRIPTION OF TRANSITION | ONSET (°C.) | MIDPOINT (°C.) | END (°C.) |
|---|---|---|---|
| Endotherm (enthalpy = 82.2 J/g) | 134 | 138 | 145 |
| Exotherm (enthalpy = −423.6 J/g) | 178 | 228 | 286 |

D. Characterization of the Dicyanate of 4'-Hydroxyphenyl-4-hydroxybenzoate for Liquid Crystallinity and Curing Behavior Using Optical Microscopy A portion of the dicyanate of 4'-hydroxyphenyl-4-hydroxybenzoate from B above is placed between two glass slides and heated from 25° to 300° C. on a hot stage at a rate of 10° C. per minute, During this heating, observations relating to changes in the morphology of the dicyanate are made at 35× magnification using a cross polarized light source, The results are given in Table XVIII,

TABLE XVIII

| OBSERVED TRANSITION TEMPERATURES (°C.) | COMMENTS |
|---|---|
| 25 | Immobile crystals. |
| 131 | Birefringent fluid, appears as crystals dispersed in fluid. |
| 137 | Isotropization complete. |
| 202 | Viscosity increases, birefringent, stir opalescent, nematic fluid. |
| 213 | Almost solid. |
| 222 | Thermosets with nematic texture. |
| 300 | Unchanged from observation at 222° C. |

EXAMPLE 13

A. Preparation of Dicyanate of bis(4'-Hydroxybenzoyl)-1,4-dihydroxybenzene bis(4'-Hydroxybenzoyl)-1,4-dihydroxybenzene (17.52 grams, 0.10 hydroxyl equivalents) from Example 12-A, cyanogen bromide (11.12 grams, 0.105 moles) and acetone (500 milliliters) are added to a reactor and maintained under a nitrogen atmosphere with stirring. The stirred solution is cooled to −2° C., then triethylamine (10.22 grams, 0.101 mole) is added to the reactor over a ten minute period and so as to maintain the reaction temperature at 0° to 2° C. After completion of the triethylamine addition, the reactor is maintained at −1° to 1° C. for an additional 45 minutes followed by addition of the reactor contents to deionized water (3.5 liters). After 2 minutes, the water and product mixture is filtered through a fritted glass funnel and the resultant cake of white powder is washed by slurrying into 300 milliliters of deionized water. A second filtration recovered the white powder which is again washed by slurrying into 300 milliliters of deionzed water. A third filtration recovered the white powder which is then dried in a vacuum oven at 80° C. and 1 mm Hg to a constant weight of 19.3 grams. Fourier transform infrared spectrophotometric analysis of a potassium bromide pellet of product confirmed the product structure (disappearance of phenolic hydroxyl absorbance, appearance of cyanate absorbance (2260 and 2293 cm−1, (sharp)).

B. Evaluation of the Curing Behavior of the Dicyanate of bis(4'-Hydroxybenzoyl)-1,4-dihydroxybenzene Using Differential Scanning Calorimetry A portion (10.0 milligrams) of the dicyanate of bis(4'-hydroxybenzoyl)-1,4-dihydroxybenzene from A above is analyzed by differential scanning calorimetry. A first heating from 30° to 300° C. is completed at a rate of 10° C. per minute under a stream of nitrogen flowing at 35 cubic centimeters per minute resulting in exothermic curing of the dicyanate. The results are given in Table XVIX. Similarly, a second heating is completed with the results given in Table XX.

TABLE XVIX

| DESCRIPTION OF TRANSITION | ONSET (°C.) | MIDPOINT (°C.) | END (°C.) |
|---|---|---|---|
| Endotherm (enthalpy = 14.6 J/g) | 90 | 99 | 111 |
| Exotherm (enthalpy = −285.7 J/g) | 118[1] | 167 | 277 |

[1]Point of first increase above baseline, sharp exothermic peak begins at 145.8° C.

TABLE XX

| | GLASS TRANSITION TEMPERATURE | | |
|---|---|---|---|
| SAMPLE DESIGNATION | ONSET (°C.) | MIDPOINT (°C.) | END (°C.) |
| Example 12-B | 178.1 | 184.5 | 192.3 |

C. Characterization of the Dicyanate of bis(4'-Hydroxybenzoyl)-1,4-dihydroxybenzene for Liquid Crystallinity and Curing Behavior Using Optical Microscopy A portion of the dicyanate of bis(4'-hydroxybenzoyl)-1,4-dihydroxybenzene from A above is placed between two glass slides and heated from 25° to 300° C. on a hot stage at a rate of 10° C. per minute. During this heating, observations relating to changes in the morphology of the dicyanate are made at 35× magnification using a cross polarized light source. The results are given in Table XXI.

TABLE XXI

| OBSERVED TRANSITION TEMPERATURES (°C.) | COMMENTS |
|---|---|
| 25 | Immobile crystals. |
| 140 | Birefringent crystalline solid softens. |
| 153 | Birefringent solid, no longer softened. |
| 300 | Unchanged from observation at 153° C. |

A second sample of the dicyanate between glass slides is introduced on to the hot stage preheated to 200° C. After seven seconds melt flow to a liquid crystalline fluid having a nematic texture is observed. After 40 seconds shear is applied to the sample by moving the top glass slide back and forth. With the application of shear, birefringent striations are observed which are oriented in the direction perpendicular to the direction that shear is applied. After 70 seconds, the sample solidifies with retention of the oriented birefringent striations.

EXAMPLE 14

Preparation of a Cured Polytriazine Casting from the Dicyanate of 4'-Hydroxyphenyl-4-hydroxybenzoate An eleven gram portion of a dicyanate of 4'-hydroxyphenyl-4-hydroxybenzoate prepared using the method of Example 12-B is placed in a beaker then put in a forced air convection type oven preheated to 160° C.

Nine minutes later, after melting is complete, the resin is degassed using a vacuum bell jar then poured into a mold which is preheated to 160° C. and has the following dimensions: 4.0×0.75×0.125 inches (102×19.0×3.17 mm). The filled mold is placed in an oven and maintained at 160° C. for 2 hours. After this time, the oven temperature is increased 20° C. per hour until a temperature of 245° C. is achieved. The 245° C. temperature is then maintained for 3 hours followed by gradual cooling to room temperature (23° C.). The opaque, yellow colored casting is demolded and tested for flexural properties using the method of Example 1-D. The flexural strength and modulus thus obtained are 17,752 and 430,625 psi, respectively. Differential scanning calorimetry of a portion (30.0 milligrams) of the casting reveals a glass transition temperature with an onset at 245.2° C., a midpoint at 251.5° C. and an end at 255.1° C. Optical microscopy of the casting at 35× magnification using a cross polarized light source reveals large (>25 microns) smectic domains.

EXAMPLE 15

A. Preparation of an Injection Molded Cured Polytriazine Casting from the Dicyanate of 4'-Hydroxyphenyl-4-hydroxybenzoate An eight gram portion of a dicyanate of 4'-hydroxyphenyl-4-hydroxybenzoate from Example 12-B is placed in a beaker then put in a forced air convection type oven preheated to 160° C. Eleven minutes later, after melting is complete, the resin is degassed using a vacuum bell jar then poured into the reservoir of an injection molder which is preheated to 160° C. After twelve minutes in the reservoir, the resin begins to develop opacity. After seventeen minutes in the reservoir, fibers can be drawn from the molten resin with a cold spatula. After nineteen minutes in the reservoir the resin is injected through a 0.02 inch (0.508 mm) rectangular flow gate into a mold preheated to 130° C. and having the following dimensions: 3.0×0.50×0.125 inches (76.2×12.7×3.17 mm). The filled mold is placed in an oven and maintained at 130° C. for 2 hours. After this time the oven temperature is increased 10° C. per hour until a temperature of 160° C. is achieved then 20° C. per hour until a temperature of 245° C. is achieved. The 245° C. temperature is then maintained for 3 hours followed by gradual cooling to room temperature (23° C.). The casting which possess both a translucent and an opalescent phase, is demolded and tested for flexural properties using the method of Example 1-D. The flexural strength and modulus thus obtained are 14,773 and 507,613 psi. respectively. Differential scanning calorimetry of a portion (30.0 milligrams) of the casting reveals a glass transition temperature with an onset at 246.9° C., a midpoint at 251.2° C. and an end at 256.1° C. Optical microscopy of the casting at 35× magnification using a cross polarized light source reveals liquid crystal textures. Optical microscopy at 35× magnification using a cross polarized light source of a sample of the 160° C. resin which is removed from the reservoir at the time of injection into the mold and placed between two glass slides on the hot stage preheated to 160° C. reveals the presence of liquid crystal texture. At this time, shear is applied to the sample by moving the top glass slide back and forth. With the application of shear, orientation is observed in the direction perpendicular to the direction that shear is applied. When cooled to 140° C., shear is again applied to the barely mobile resin and results in orientation both parallel and transverse to the direction that shear is applied.

B. Thermal Mechanical Analysis of the Injection Molded Cured Polytriazine Casting of the Dicyanate of 4'-Hydroxyphenyl-4-Hydroxybenzoate Cubes measuring 0.125 inch (3.17 mm) are cut from the injection molded casting prepared in A above then used in thermal mechanical analysis. In this analysis, a constant probe force of 0.1 Newtons and a heating rate of 5° C. per minute is used over a range of 40° to 225° C. The mean linear coefficients of thermal expansion obtained from the analyses are as follows: 97 ppm/°C. for the z coordinate (surface of the casting), 35 ppm/°C. for the y coordinate (flow direction) and 91 ppm/°C. for the x direction (transverse to the flow direction). The substantially lower mean linear coefficient of thermal expansion in the direction of the y coordinate demonstrates the anisotropy which can be produced by processing methods that induce shear, such as injection molding.

What is claimed is:

1. A polycyanate or polycyanamide composition containing one or more rodlike mesogenic moieties represented by the following Formulas I, II, III or IV

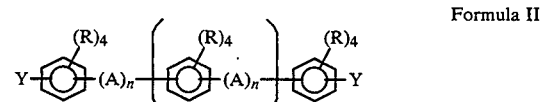

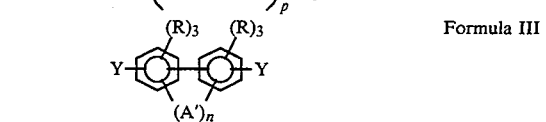

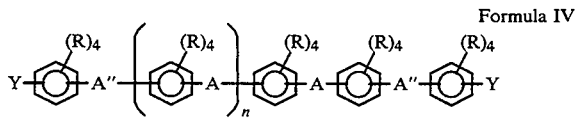

wherein at least about 80 percent of the —A— linkages, the direct bond in Formula III and the Y groups are in the para position with respect to each other; each Y is independently a —O—C≡N or a —NR$^1$—C≡N group; each A in Formula II when p is 1 is independently —CR$^1$=CR$^1$—, —C≡C—, —N=N—, —CR$^1$=N—, —NR$^1$—CO—, —CR$^1$=N—N=CR$^1$—, —CR$^1$=CR$^1$—CO—, —CO—NR$^1$—, —CO—CR$^1$=CR$^1$—, —CR$^1$=CR$^1$—O—CO—(CH$_2$)$_{n'}$—, —N=CR$^1$—, —(CH$_2$)$_{n'}$—CO—O—CR$^1$=CR$^1$—, —CR$^1$=CR$^1$—O—CO—, —CO—O—CR$^1$=CR$^1$—, —CO—O—N=CR$^1$—, —CR$^1$=N—O—CO—, —CR$^1$=CR$^1$—CO—O—, —CO—S—, —O—CO—CR$^1$=CR$^1$, —CR$^1$=CR$^1$—CO—O—(CH$_2$)$_{n'}$—, —S—CO—, —(CH$_2$)$_{n'}$—O—CO—CR$^1$=CR$^1$—, —CHR$^1$—CHR$^1$—CO—O—, —O—CO—CHR$^1$—CHR$^1$—, —C≡C—C≡C—, —CR$^1$=CR$^1$—CR$^1$=CR$^1$—, —CO—NR$^1$—NR$^1$—CO—,

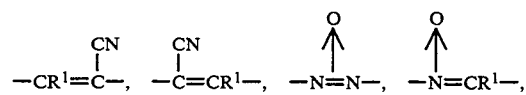

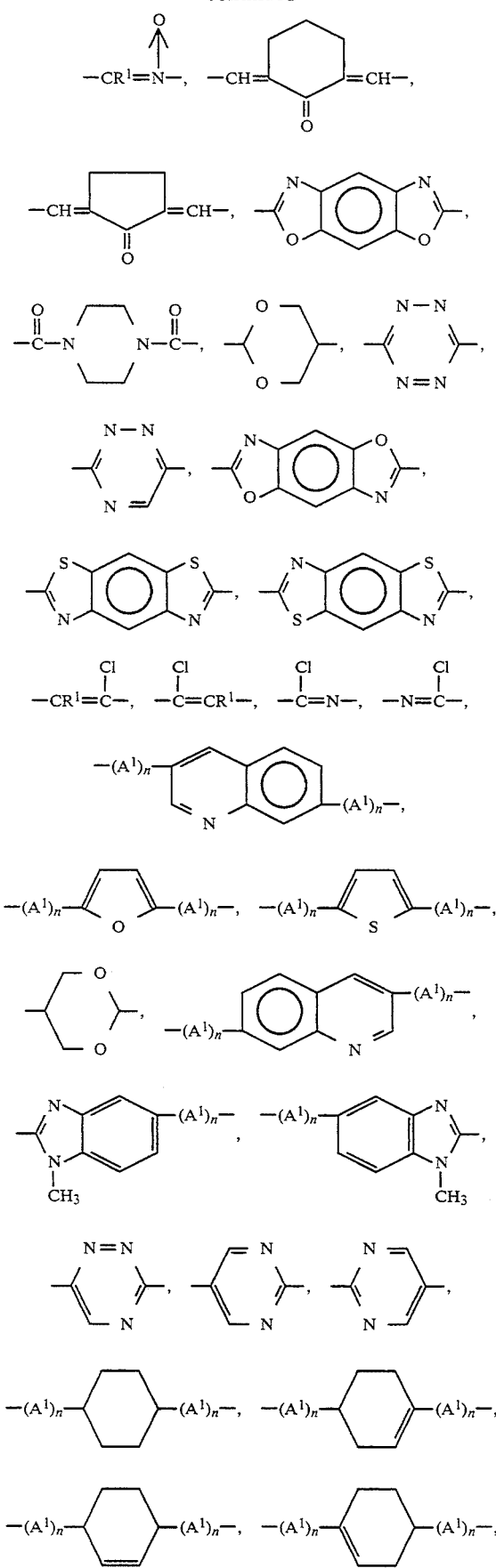
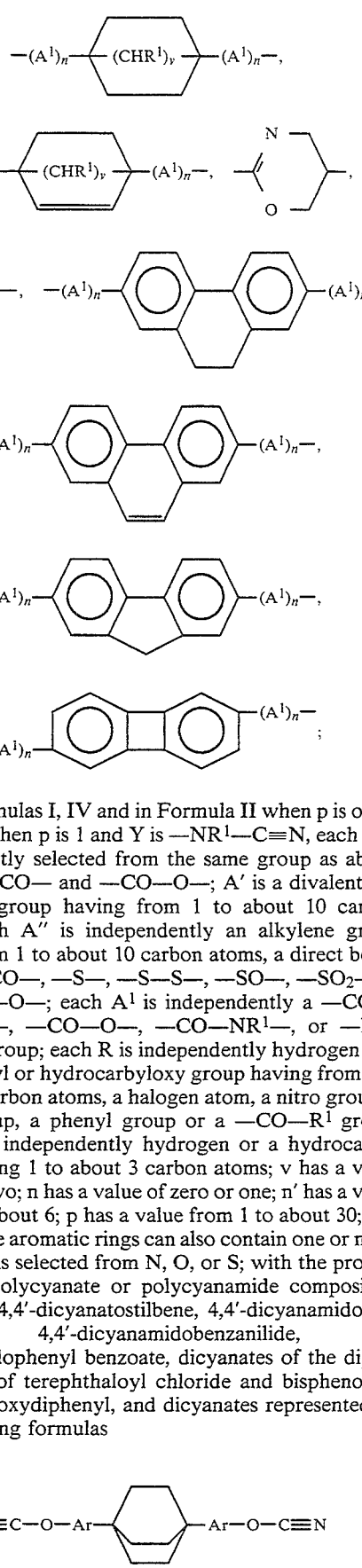

and in Formulas I, IV and in Formula II when p is other than 1 or when p is 1 and Y is —NR$^1$—C≡N, each A is independently selected from the same group as above plus —O—CO— and —CO—O—; A' is a divalent hydrocarbyl group having from 1 to about 10 carbon atoms; each A" is independently an alkylene group having from 1 to about 10 carbon atoms, a direct bond, —O—, —CO—, —S—, —S—S—, —SO—, —SO$_2$— or —O—CO—O—; each A$^1$ is independently a —CO—, —O—CO—, —CO—O—, —CO—NR$^1$—, or —NR$^1$—CO— group; each R is independently hydrogen or a hydrocarbyl or hydrocarbyloxy group having from 1 to about 10 carbon atoms, a halogen atom, a nitro group, a nitrile group, a phenyl group or a —CO—R$^1$ group; each R$^1$ is independently hydrogen or a hydrocarbyl group having 1 to about 3 carbon atoms; v has a value of one to two; n has a value of zero or one; n' has a value from 1 to about 6; p has a value from 1 to about 30; and wherein the aromatic rings can also contain one or more heteroatoms selected from N, O, or S; with the proviso that said polycyanate or polycyanamide composition cannot be 4,4'-dicyanatostilbene, 4,4'-dicyanamidoazobenzene, 4,4'-dicyanamidobenzanilide, 4,4'-dicyanamidophenyl benzoate, dicyanates of the diphenol esters of terephthaloyl chloride and bisphenol A, 4,4'-dihydroxydiphenyl, and dicyanates represented by the following formulas -continued
or

wherein Ar is an aromatic radical selected from the group consisting of 1,4'-benzene, 1,4-naphthalene, 1,5-naphthalene, 2,6-naphthalene, 2,7-naphthalene, 4,4'-biphenyl or 4,4'-diphenylalkylene radicals and can possess any nonactive hydrogen-containing substituent(s) which do not remove mesogenicity.

2. A polycyanate or polycyanamide composition of claim 1 wherein said polycyanate or polycyanamide is the dicyanate of 4,4'-dihydroxy-α-methylstilbene, the dicyanate of bis(4'-hydroxyphenyl)-1,4-benzenediimine, the dicyanate of 4,4'-dihydroxybenzanilide, the dicyanate of 4'-hydroxyphenyl-4-hydroxybenzoate, the dicyanate of bis(4'-hydroxybenzoyl)-1,4-dihydroxybenzene, or any combination thereof.

* * * * *

UNITED STATES PATENT AND TRADEMARK OFFICE
CERTIFICATE OF CORRECTION

PATENT NO. : 5,428,125
DATED : June 27, 1995
INVENTOR(S) : Robert E. Hefner, Jr. et al.

It is certified that error appears in the above-indentified patent and that said Letters Patent is hereby corrected as shown below:

In claim 1, column 67, line 10, "group consisting of 1,4'-benzene," should read --group consisting of 1,4-benzene, --.

Signed and Sealed this

Fifteenth Day of July, 1997

Attest:

Attesting Officer

BRUCE LEHMAN

Commissioner of Patents and Trademarks